(12) United States Patent
Gokaraju et al.

(10) Patent No.: US 11,684,648 B2
(45) Date of Patent: Jun. 27, 2023

(54) SYNERGISTIC HERBAL COMPOSITIONS FOR TESTOSTERONE BOOSTING

(71) Applicant: LAILA NUTRACEUTICALS, Vijayawada (IN)

(72) Inventors: Ganga Raju Gokaraju, Vijaywada (IN); Rama Raju Gokaraju, Vijayawada (IN); Trimurtulu Golakoti, Vijayawada (IN); Kiran Bhupathiraju, Vijayawada (IN); Venkata Kanaka Ranga Raju Gokaraju, Vijayawada (IN); Krishanu Senguptha, Vijayawada (IN); Venkata Krishna Raju Alluri, Vijayawada (IN); Venkateswarlu Somepalli, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 585 days.

(21) Appl. No.: 16/492,473

(22) PCT Filed: Mar. 8, 2018

(86) PCT No.: PCT/IN2018/050132
§ 371 (c)(1),
(2) Date: Sep. 9, 2019

(87) PCT Pub. No.: WO2018/163214
PCT Pub. Date: Sep. 13, 2018

(65) Prior Publication Data
US 2021/0138014 A1      May 13, 2021

(30) Foreign Application Priority Data

Mar. 8, 2017   (IN) .............................. 201741008126
Nov. 18, 2017  (IN) .............................. 201741041318

(51) Int. Cl.
| | |
|---|---|
| *A61K 36/54* | (2006.01) |
| *A61K 36/22* | (2006.01) |
| *A61K 36/31* | (2006.01) |
| *A61K 36/71* | (2006.01) |
| *A61K 36/8962* | (2006.01) |
| *A61P 5/24* | (2006.01) |
| *A61K 36/48* | (2006.01) |

(52) U.S. Cl.
CPC .............. *A61K 36/54* (2013.01); *A61K 36/22* (2013.01); *A61K 36/31* (2013.01); *A61K 36/71* (2013.01); *A61K 36/8962* (2013.01); *A61P 5/24* (2018.01); *A61K 36/48* (2013.01); *A61K 2300/00* (2013.01)

(58) Field of Classification Search
None
See application file for complete search history.

(56) References Cited

U.S. PATENT DOCUMENTS

| | | |
|---|---|---|
| 5,543,146 A | 8/1996 | Perez |
| 2014/0086999 A1 | 3/2014 | Elistratov |

FOREIGN PATENT DOCUMENTS

| | | |
|---|---|---|
| WO | 2011/026500 A1 | 3/2011 |

OTHER PUBLICATIONS

Mohajeri D., et al., Effects of Nigella sativa on heat-induced testis damage in mouse, Abstract, Bratislavske Lekarske Listy, Jan. 1, 2015, 116(4):264-269.*
Tahvilzadeh, M., et al., An evidence-based approach to medicinal plants for the treatment of sperm abnormalities in traditional Persian medicine, Andrologia 2016; 48: 860-879.*
Khaki, A., et al., Evaluation of androgenic activity of allium cepa on spermatogenesis in the rat, Folia Morphol. (2009) vol. 68, No. 1, pp. 45-51.*

* cited by examiner

*Primary Examiner* — H. Sarah Park
(74) *Attorney, Agent, or Firm* — Kramer & Amado, P.C.

(57) ABSTRACT

Synergistic herbal compositions for Testosterone boosting comprising at least two ingredients selected from the extracts, fractions or pure phytochemicals derived from *Punica granatum, Cinnamomum zeylanicum, Nigella sativa, Brassica nigra* and *Mangifera indica* for improving testosterone levels and alleviating symptoms associated with low levels of testosterone hormone in humans. The present invention also describes a synergistic composition comprising at least one testosterone booster ingredient selected from the extracts, fractions or pure phytochemical derived from *Punica granatum, Cinnamomum zeylanicum, Nigella sativa, Brassica nigra* and *Mangifera indica* and at least one aromatase inhibitor ingredient selected from the extracts, fractions or pure phytochemicals derived from *Allium cepa, Tamarindus indica* and *Cinnamomum tamala* for improving testosterone levels and alleviating symptoms associated with low levels of testosterone hormone in humans. The invention further provides methods of improving testosterone levels and alleviating symptoms associated with low levels of testosterone hormone in humans.

15 Claims, 1 Drawing Sheet

SYNERGISTIC HERBAL COMPOSITIONS FOR TESTOSTERONE BOOSTING

TECHNICAL FIELD OF THE INVENTION

The invention relates to synergistic herbal compositions comprising extracts or fractions derived from at least two herbs selected from *Punica granatum, Cinnamomum zeylanicum, Nigella sativa, Brassica nigra* and *Mangifera indica* for improving testosterone levels in humans and alleviating at least one symptom(s)/conditions associated with lower than normal levels of testosterone hormone in humans. The invention further relates to synergistic herbal compositions comprising an extract or fraction derived from at least one testosterone booster herb selected from *Punica granatum, Cinnamomum zeylanicum, Nigella sativa, Brassica nigra* and *Mangifera indica* and extract or fraction derived from at least one aromatase inhibitor herb selected from *Allium cepa, Tamarindus indica* or *Cinnamomum tamala* for improving testosterone levels in humans and alleviating at least one symptom(s)/conditions associated with low levels of testosterone hormone in humans. The invention also relates to the methods of improving testosterone levels in humans and methods of alleviating symptoms associated with low levels of testosterone hormone in humans.

BACKGROUND OF THE INVENTION

Testosterone is a hormone chemical messenger produced primarily by Leydig cells in testes/testicles and is responsible for the proper development of male sexual characteristics. It is a type of androgen essential for the process of spermatogenesis. Testosterone is known to regulate a number of functions in men in addition to sperm production, which include sex drive, bone mass, muscle size and strength etc. As men age, the serum testosterone levels gradually decrease every year, resulting in various physical and mental changes such as loss of libido, erectile dysfunction, abdominal obesity, decreased muscle mass and strength, decreased bone density, decreased motivation, and decreased memory and concentration.

Many Testosterone replacement therapies are available to treat the men suffering from testosterone deficiency, which include dehydroepiandrosterone (DHEA), and herbal products such as *Tribulus terrestris*. The low levels of testosterone were found to be associated with significantly lower levels of magnesium, iron, and zinc. Hence, supplements containing these nutrients are also available as testosterone boosters.

The patent publication WO2011026500 A1, discloses compositions comprising extracts of *Tribulus terrestris* and *Lepidium meyenii* for the treatment of erectile dysfunction by increasing testosterone levels.

The patent publication US 20140086999 A1, discloses a biologically active dietary supplement for normalizing the androgen levels in men, improving general health and reducing obesity, said dietary supplement comprises roots and rhizomes of white cinquefoil, or aerial portions of white cinquefoil, or mixture thereof; and drone brood in the weight proportion of: from 20 wt % to 80 wt %.

Another patent publication U.S. Pat. No. 5,543,146 A, discloses a dietary supplement for alleviating the symptoms associated with enlargement of the prostate gland, comprising the following ingredients: pumpkin seeds in an amount of between 12.50 to 25% by weight of the composition; Extract of *Serenoa repens* in an amount of between 1.875 to 18.75% by weight of the composition; *Pygeum africanum* in an amount of between 6.25 to 12.5% by weight of the composition; zinc glycinate in an amount of between 3.125 to 6.25% by weight of the composition; and excipients, wherein the amount of ingredients in the dietary supplement totals 100%.

One of the key reasons for the reduced levels of testosterone in men is its conversion to estradiol. Aromatase is the enzyme responsible for conversion of androgens to estrogens, specifically for the conversion of testosterone into estradiol. Weight gain and aging are known to increase the loss of testosterone by this conversion. In addition, excess estradiol in men was known to be responsible for health problems related to prostate, gynocomastia and erectile dysfunction, low libido. Aromatase inhibitors are known to increase the levels of luteinizing hormone (LH), follicle-stimulating hormone (FSH) and testosterone. Hence, the aromatase inhibitors can be used as tool to enhance the testosterone levels.

Hence, there is a continuous need in the art to provide cost-effective alternative treatments comprising highly effective herbal extracts for improving concentrations of testosterone in seminal vesicle and bloodstream. Moreover, there is a need in the art for better treatment options for improving testosterone levels that provide minimal side effects thereby making the option safe for human consumption.

OBJECT OF THE INVENTION

Therefore, the object of the present invention is to provide synergistic and safe herbal compositions comprising extracts, fractions or pure compounds derived from at least two herbs selected from *Punica granatum, Cinnamomum zeylanicum, Nigella sativa, Brassica nigra* and *Mangifera indica* for improving concentrations of testosterone in both seminal vesicle and bloodstream and for alleviating at least one symptom(s) associated with the low levels of testosterone in human males such as loss of libido, erectile dysfunction, abdominal obesity, decreased muscle mass and strength, decreased bone density, decreased motivation, and decreased memory & concentration and improve the feelings of well-being.

Another object of the present invention is to provide synergistic herbal compositions comprising extract(s) or fraction(s) derived from at least one testosterone booster herb selected from *Punica granatum, Cinnamomum zeylanicum, Nigella sativa, Brassica nigra* and *Mangifera indica* and extract(s) or fraction(s) derived from at least one aromatase inhibitor herb selected from *Allium cepa, Tamarindus indica* or *Cinnamomum tamala* for improving concentrations of testosterone in both seminal vesicle and bloodstream in humans and to treat/alleviate the symptoms associated with the low levels of testosterone such as loss of libido, erectile dysfunction, abdominal obesity, decreased muscle mass and strength, decreased bone density, decreased motivation, and decreased memory & concentration and improve the feelings of well-being.

Yet another objective of the invention is to provide use of the synergistic herbal compositions of the present inventions for increasing the testosterone levels thereby treating/alleviating the symptoms associated with the low levels of testosterone. Further objective of the invention is to provide methods of treating/alleviating the symptoms associated with the low levels of testosterone in humans using the synergistic herbal compositions of the present inventions.

SUMMARY OF THE INVENTION

The present invention provides synergistic herbal compositions comprising the extracts, fractions or pure compounds derived from at least two herbs selected from *Punica granatum*, *Cinnamomum zeylanicum*, *Nigella sativa*, *Brassica nigra* and *Mangifera indica* for boosting the concentrations of testosterone in humans.

One aspect of the invention provides the use of synergistic herbal compositions comprising extracts, fractions or pure compounds derived from at least two herbs selected from *Punica granatum*, *Cinnamomum zeylanicum*, *Nigella sativa*, *Brassica nigra* and *Mangifera indica* to increase testosterone levels, and to treat erectile dysfunction, improve sexual function, improve energy, enhance feelings of well-being and increase muscle mass in males.

Other aspect of the invention provides methods of improving testosterone levels in humans, and treating/alleviating symptoms associated with low levels of testosterone such as loss of libido, erectile dysfunction, abdominal obesity, decreased muscle mass and strength, decreased bone density, decreased motivation, and decreased memory and concentration in a humans wherein the method comprises supplementing humans with an effective dose of a synergistic herbal composition comprising extracts, fractions or pure compounds derived from at least two herbs selected from *Punica granatum*, *Cinnamomum zeylanicum*, *Nigella sativa*, *Brassica nigra* and *Mangifera indica*.

Yet another aspect of the invention provides methods of improving testosterone levels in humans, and treating/alleviating symptoms associated with low levels of testosterone such as loss of libido, erectile dysfunction, abdominal obesity, decreased muscle mass and strength, decreased bone density, decreased motivation, and decreased memory and concentration in a human wherein the method comprises supplementing humans with an effective dose of a synergistic composition comprising the extracts, fractions or pure compounds derived from at least two herbs selected from *Punica granatum*, *Cinnamomum zeylanicum*, *Nigella sativa*, *Brassica nigra* and *Mangifera indica*; and optionally containing at least one additional ingredient selected from pharmaceutically acceptable excipient, pharmaceutically acceptable diluent, and pharmaceutically acceptable carrier.

The present invention also provides synergistic herbal compositions comprising extract(s) or fraction(s) derived from at least one testosterone booster herb selected from *Punica granatum*, *Cinnamomum zeylanicum*, *Nigella sativa*, *Brassica nigra* and *Mangifera indica* and extract(s) or fraction(s) derived from at least one aromatase inhibitor herb selected from *Allium cepa*, *Tamarindus indica* or *Cinnamomum tamala* for boosting the concentrations of testosterone in humans. Other aspect of the invention provides the use of synergistic herbal compositions comprising extract(s) or fraction(s) derived from at least one testosterone booster herb selected from *Punica granatum*, *Cinnamomum zeylanicum*, *Nigella sativa*, *Brassica nigra* and *Mangifera indica* and extract(s) or fraction(s) derived from at least one aromatase inhibitor herb selected from *Allium cepa*, *Tamarindus indica* or *Cinnamomum tamala* for increasing testosterone levels, treating sexual dysfunction, improving sexual function, improving energy, enhancing feelings of well-being and increasing muscle mass in males.

Other aspect of the invention provides methods of improving testosterone levels in humans, and treating/alleviating symptoms associated with low levels of testosterone such as loss of libido, erectile dysfunction, abdominal obesity, decreased muscle mass and strength, decreased bone density, decreased motivation, and decreased memory and concentration in a human wherein the method comprises supplementing humans with an effective dose of a composition comprising extract(s) or fraction(s) derived from at least one testosterone booster herb selected from *Punica granatum*, *Cinnamomum zeylanicum*, *Nigella sativa*, *Brassica nigra* and *Mangifera indica* and extract(s) or fraction(s) derived from at least one aromatase inhibitor herb selected from *Allium cepa*, *Tamarindus indica* or *Cinnamomum tamala*.

Yet other aspect of the invention provides methods of improving testosterone levels in humans, and treating/alleviating at least one symptom(s) associated with low levels of testosterone such as loss of libido, erectile dysfunction, low sperm count, abdominal obesity, decreased muscle mass and strength, decreased bone density, decreased motivation, and decreased memory and concentration in a human wherein the method comprises supplementing humans with an effective dose of a composition comprising extract(s) or fraction(s) derived from at least one testosterone booster herb selected from *Punica granatum*, *Cinnamomum zeylanicum* *Nigella sativa*, *Brassica nigra*, and *Mangifera indica* and extract(s) or fraction(s) derived from at least one aromatase inhibitor herb selected from *Allium cepa*, *Tamarindus indica* or *Cinnamomum tamala*; and optionally containing at least one ingredient selected from pharmaceutically/dietically acceptable excipient, pharmaceutically acceptable diluent, and pharmaceutically acceptable carrier.

DESCRIPTION OF THE INVENTION

Figure 1:
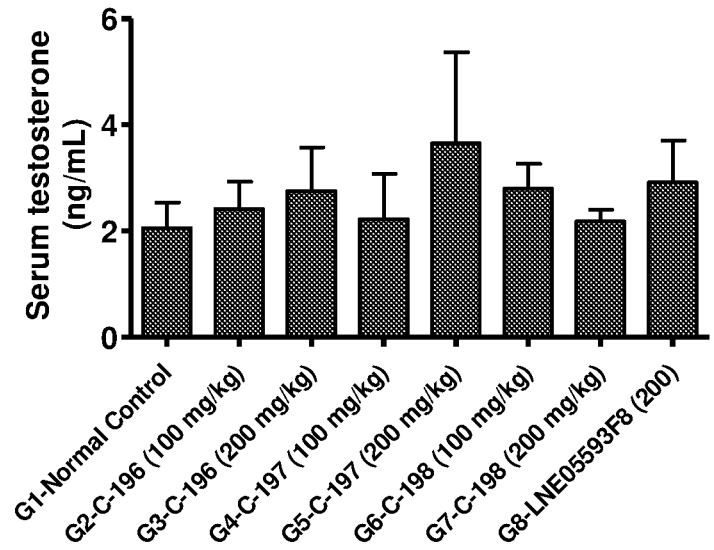
FIG. 1: The bar chart represents serum testosterone level (ng/mL) on day 43 in control group (G1) and treatment groups, G2 to G8 and each bar represent mean ± S.E.M and n=7.

Testosterone is a key androgenic male hormone and it is primarily produced by testis in Leydig cells. Testosterone is responsible for the development of male reproductive tissues and promoting secondary sexual characteristics. In adult males, testosterone is responsible for the maintenance of muscle and bone mass, sexual function and psychological well-being. The testosterone levels gradually decline as men age and the undesirable effects associated with this condition, called 'andropause, have been receiving increased attention in recent years. The undesirable effects include decreased desire for sex (libido), diminished erectile quality, particularly for night time erections, changes in mood, reduced intellectual and cognitive function, fatigue, depression, and anger, decrease in muscle mass and strength, decreased body hair, skin alterations, erectile dysfunction, low sperm count, abdominal obesity, decreased memory and concentration, decreased bone mass/mineral density, increase in abdominal fat mass.

Male hypogonadism is defined by the Endocrine Society as a clinical syndrome that results from the inability of the testes to produce physiologic levels of testosterone (T) and a 'normal_number of spermatozoa secondary to a dysfunction in the hypothalamic-pituitary-gonadal axis (HPG) (Bhasin S, et al., J. Clin. Endocrinol. Metab. 2010; 95: 2536.). A consensus statement from the International Society of Andrology (ISA), the International Society for Study of the Aging Male (ISSAM), the European Association of Urology (EAU), the European Association of Andrology (EAA) and the American Society of Andrology (ASA) recommended that total testosterone (TT) levels above 350 ng/dL do not require treatment, and levels below 230 ng/dL (with symptoms) may require T replacement therapy (Wang C, et al., J. Androl. 2009; 30: 1). Similarly, it has been previously recommended that men with TT<200 ng/dL be treated as hypogonadal, those with TT>400 ng/dL be considered normal and those with TT 200-400 ng/dL be treated based on their clinical presentation if symptomatic (Hellstrom J G, et al., Int. Urol. Nephrol. 2012; 44: 61). Many Testosterone replacement therapies are available to treat the men suffering from testosterone deficiency but each of them has its own disadvantages. (Nazem Bassil, et al., Ther Clin Risk Manag. 2009; 5: 427-448. Published online 2009 Jun. 22).

Hence the inventors of the current application randomly screened a large number of plant extracts and fractions for their testosterone boosting activity in in vitro cellular model using MA-10 mouse leydig cell line and found that the extracts and fractions derived from *Punica granatum, Cinnamomum zeylanicum, Nigella sativa, Brassica nigra* and *Mangifera indica* showed a potent dose dependent testosterone boosting activity as summarized in tables 2-13.

Source of the herbs used in the invention as follows:—
1) *Punica granatum* collected from Kothacheruvu village, Kothacheruvu mandal, Ananthpur district, Andhra Pradesh.
2) *Cinnamomum zeylanicum* imported from Sri Ianka.
3) *Nigella sativa* collected from Himachal Pradesh.
4) *Brassica nigra* Collected from Madhya Pradesh.
5) *Mangifera indica* collected from Nuzividu, Krishna District, and Andhra Pradesh.
6) *Allium cepa* collected from Kalluru village, Lepakshi Mandal, Ananthpur district, Andhra Pradesh.
7) *Tamarindus indica* collected from Hanumanthulagudem village, Nuzvidu mandal, Krishna district, Andhra Pradesh.
8) *Cinnamomum tamla* collected from Assam state.

Thus *Punica granatum* fruit rind ethanol extract (P.G-1) for example at the treatment concentrations of 25 ng/mL showed 27.02% increase in testosterone respectively over control. The *Nigella sativa* seed/fruit water extract (N.S-1) at the treatment concentration of 25 mg/mL showed 34.05% increase in testosterone respectively over control. Similarly, *Brassica nigra* seed ethanol extract (B.N-1) at the treatment concentrations of 25 mg/mL showed 37.8%, *Cinnamomum zeylanicum* bark ethanol extract (C.Z-1) at 5 mg/mL concentration showed 15.14% and *Mangifera indica* bark 50% ethanol extract (M.I-1) at 5 mg/mL concentration showed 30.15% increase in testosterone respectively over control.

These individual extracts or their fractions were then evaluated to explore the feasibility of obtaining synergistic efficacy, when the individual extracts or fractions are combined.

Thus, at least two ingredients selected from the extracts, fractions and pure compounds, each derived from different herbal raw material selected from *Punica granatum, Cinnamomum zeylanicum, Nigella sativa, Brassica nigra* and *Mangifera indica* were combined at different ratios and the compositions so obtained (compositions 1-110) were tested for testosterone boosting activity along with the corresponding individual ingredients. The data from in vitro testosterone assay for these compositions as summarized in Tables 2 to 13 unexpectedly showed better efficacy in increasing testosterone levels when compared to their corresponding individual ingredients suggesting that these individual extracts and fractions have the tendency to exhibit synergism when combined together.

For example, *Punica granatum* rind ethanol extract (P.G-1) and *Cinnamomum zeylanicum* bark ethanol extract (C.Z-1) at 2.51 g/mL showed 8.1% and 4.55% increase in testosterone concentrations respectively in cellular assay. The composition-3 containing these two extracts at 1:1 ratio showed 22.58% increase in testosterone at 5 mg/mL concentration, which is significantly better than the additive effect (8.1%+4.55%=12.65%) from these two ingredients, suggesting synergistic effect in enhancing the testosterone levels by *Punica granatum* rind ethanol extract (P.G-1) and *Cinnamomum zeylanicum* bark ethanol extract (C.Z-1). These two ingredients also showed synergism when combined at ratios, 1:3, 1:2, 2:1 and 3:1 as shown by the superior testosterone enhancing effects exhibited by the compositions-1, 2, 4 and 5 respectively as summarized in Table 2. Similarly, the compositions (Compositions-6 to 19) containing other solvent extracts of *Punica granatum* rind and *Cinnamomum zeylanicum* bark also exhibited synergistic properties. For illustration, the compositions-6, 7, 8 and 9 containing *Punica granatum* fruit rind 70% ethanol extract (P.G-4) in combination with *Cinnamomum zeylanicum* bark 90% ethanol extract (C.Z-2) at ratios 3:1, 2:1, 1:1 and 1:2 showed synergistic effects with increased testosterone levels of 19.26%, 15.72%, 21.68% and 23.30% respectively over the control, which are significantly higher than the additive effects calculated for each of these compositions from the corresponding testosterone improvements shown by the individual ingredients. In addition, the compositions-17 and 19 containing *Punica granatum* fruit rind water extract (P.G-6) and *Cinnamomum zeylanicum* bark water extract (C.Z-4) at ratios 2:1 and 1:2 also showed synergistic effects with improved testosterone levels of 24.48% and 30.09% respectively, when compared to the corresponding additive effects 18.31% and 19.05% contributed from the individual ingredients. The results for the foregoing studies are summarized in Table 2.

Interestingly, *Punica granatum* rind extract also exhibited synergism when combined with other plant derived ingredients as illustrated hereinafter with the extracts produced from *Nigella sativa* or *Brassica nigra*. For example, *Punica granatum* rind ethanol extract (PG-1) and *Nigella sativa* seed/fruit water extract (N.S-1) showed 8.1% and 6.64% increase in testosterone levels respectively at 2.5 mg/mL. The composition-23 (C-23) containing these two extracts at 1:1 ratio showed significantly better efficacy with 25.37% improvement in testosterone levels at 5 mg/mL concentration, which is better than the additive effect (8.1%+ 6.64%=14.74%) from these two ingredients, suggesting synergistic effect between *Punica granatum* rind ethanol extract (P.G-1) and *Nigella sativa* water extract (N.S-1). These two ingredients also showed synergism when combined at other ratios, 1:2, 2:1 and 3:1 as shown by the improved testosterone levels exhibited by the compositions-22, 24 and 25 respectively as summarized in Table 3. The other solvent extracts of *Punica granatum* rind also showed synergism with *Nigella sativa* extracts. The composition-26 to composition-30 containing 70% ethanol extract of *Punica granatum* rind (P.G-4) and water extract of *Nigella sativa* (N.S-1) at 3:1, 2:1, 1:1, 1:2 and 1:3 ratios respectively; and Composition-32 to composition-34 containing water extract of *Punica granatum* rind (P.G-6) and water extract of *Nigella sativa* (N.S-1) at 2:1, 1:1 and 1:2 ratio respectively also exhibited synergism as summarized in Table 3.

Similarly, the composition containing extracts of *Punica granatum* rind and *Brassica nigra* also manifested synergistic association as demonstrated henceforth by the improved efficacy observed for their compositions. For example, the composition-40 containing *Punica granatum* rind ethanol extract (P.G-1) and *Brassica nigra* seed ethanol extract (B.N-1) at 3:1 ratio showed 23.27% increase in testosterone levels at 5 mg/mL treatment concentration, which is better than the additive effect (12.15%+4.15%=16.3%) calculated from the improvements shown by the individual ingredients suggesting synergistic effect. Likewise, the compositions-41, 42, 43 and 44 containing the 70% ethanol extract of *Punica granatum* rind (P.G-4) and 90% ethanol extract of *Brassica nigra* (B.N-2) at 3:1, 2:1, 1:1 and 1:2 ratios respectively; compositions-47, 48 and 49 containing water extract of *Punica granatum* rind (P.G-6) and water extract of *Brassica nigra* (B.N-4) at 2:1, 1:1 and 1:2 ratios respectively; compositions-52, 53 and 54 containing methanol extract of *Punica granatum* rind (P.G-7) and water extract of *Brassica nigra* (B.N-4) at 2:1, 1:1 and 1:2 respectively and compositions-57, 58 and 59 containing 70% ethanol extract of *Punica granatum* rind (P.G-4) and methanol extract of *Brassica nigra* (B.N-5) at 2:1, 1:1, 1:2 respectively also showed significantly better enhancements in testosterone levels compared to the corresponding additive effects as summarized in Table 4 suggesting synergistic efficacy for all the compositions.

Further to the above, synergistic behaviors were also observed between the extracts of *Punica granatum* rind and extracts of *Mangifera indica* bark. The compositions-62, 63 and 64 containing 70% ethanol extract of *Punica granatum* rind (P.G-4) and 50% ethanol extract of *Mangifera indica* bark (M.I-1) at extract ratios of 2:1, 1:1 and 1:2 respectively exhibited improved testosterone concentrations of 15.71%, 18.31% and 20.45%, which are far better than the additive effects calculated from the testosterone concentrations obtained for the corresponding individual ingredients. The compositions-67, 68 and 69 containing water extract of *Punica granatum* (P.G-6) rind and water extract of *Mangifera indica* bark (M.I-3) at 2:1, 1:1 and 1:2 respectively also showed synergistic effects as summarized in Table 5. In addition to the testosterone boosting effects disclosed above for the extracts of *Punica granatum* synergism efficacy was also observed when an extract derived from *Cinnamomum zeylanicum* was combined with an extract derived from *Brassica nigra*, *Nigella sativa*, or *Mangifera indica*. For example, compositions-77 and 79 containing *Cinnamomum zeylanicum* bark 90% ethanol extract (C.Z-2) and *Brassica nigra* seed 90% ethanol extract (B.N-2) at 2:1 and 1:2 ratios respectively showed better testosterone levels (13.81% and 15.38%) than the corresponding additive effects (5.89% and 9.00%). The compositions-74 and 75 containing *Cinnamomum zeylanicum* bark ethanol extract (C.Z-1) and *Brassica nigra* seed ethanol extract (B.N-1) at 2:1 and 3:1 ratio; the compositions-81, 82, 83, 84 and 85 containing *Cinnamomum zeylanicum* bark 90% ethanol extract (C.Z-2) and *Nigella sativa* fruit/seed water extract (N.S-1) at 3:1, 2:1, 1:1, 1:2 and 1:3 respectively; and compositions-87, 88 and 89 containing *Cinnamomum zeylanicum* bark 90% ethanol extract (C.Z-2) and *Mangifera indica* 50% ethanol extract (M.I-1) at 2:1, 1:1 and 1:2 ratios respectively also showed synergistic improvements in testosterone levels as summarized in Table 6.

Further, synergism efficacy was also observed when an extract derived from *Nigella sativa* was combined with an extract derived from *Brassica nigra* or *Mangifera indica*. For example the compositions-91, 93 and 94 containing *Nigella sativa* water extract (N.S-1) and *Brassica nigra* ethanol extract (B.N-1) in 3:1, 1:1 and 1:2 ratios manifested testosterone improvements of 13.8%, 23.93% and 14.46% respectively over the control, which are over and above the additive effects 8.05%, 14.95% and 9.71% calculated from the testosterone improvements shown by the corresponding individual ingredients in the compositions as summarized in table 7. Similarly, the compositions-97, 98 and 99 containing *Nigella sativa* water extract (N.S-1) and *Brassica nigra* 90% ethanol extract (B.N-2) in 2:1, 1:1 and 1:2 ratios respectively and the compositions-102, 103 and 104 containing *Nigella sativa* water extract (N.S-1) and *Mangifera indica* 50% ethanol extract (M.I-1) in 2:1, 1:1 and 1:2 ratios respectively also showed synergistic improvements in testosterone levels as summarized in Table 7.

Finally, synergistic efficacy was also observed when an extract derived from *Brassica nigra* was combined with an extract derived from *Mangifera indica*. For example, the compositions-107, 108 and 109 containing *Brassica nigra* ethanol extract (B.N-1) and *Mangifera indica* 50% ethanol extract (M.I-1) at ratios 2:1, 1:1 and 1:2 respectively showed superior increase in testosterone levels compared to the corresponding additive effects as summarized in Table 8.

The key reasons for low levels of testosterone include disorders of pituitary and hypothalamus glands, mental and physical stress, aging, medications, concurrent illness etc. More than normal levels of testosterone is required for increasing the sexual drive, libido, enhancing muscle strength and muscle mass. The other key reason for the reduced levels of testosterone in men is its conversion to estradiol. Aromatase is the enzyme responsible for the conversion of androgens to estrogens, specifically for the conversion of testosterone into estradiol. Hence, the aromatase inhibitors can be used as a tool to inhibit the conversion of testosterone, thereby enhancing its levels in biological systems. Supplementation of aromatase inhibitors is known to increase the levels of LH, follicle-stimulating hormone (FSH) and testosterone. The inventors thus envisaged that a testosterone boosting herbal ingredient can work in tandem with an aromatase inhibiting herbal ingredient and their compositions can show better testosterone boosting activity when compared to the individual ingredients.

Hence, the inventors of the current application randomly screened a large number of plant extracts for their aromatase inhibition activity and found that the extracts derived from *Allium cepa*, *Tamarindus indica* or *Cinnamomum tamala* showed potent dose dependent aromatase inhibition activity. Thus *Allium cepa* bulb water extract (A.C-1) for example at the treatment concentrations of 1.25 and 2.5 mg/mL showed 3.13% and 6.26% aromatase inhibitions respectively. Similarly, the juice concentrate (A.C-4) of *Allium cepa* bulb at the treatment concentration of 1.0 and 3.3 mg/mL also showed 27.1 and 35.3% aromatase inhibition respectively. Similarly, *Tamarindus indica* seed ethanol extract (T.I-1) at the treatment concentration of 1.0 and 3.3 mg/mL showed 29.5% and 39.2% inhibition of aromatase activity and *Cinnamomum tamala* leaves methanol extract (C.T-2) at the treatment concentrations 1.0 and 3.3 mg/mL showed 31.5% and 39.0% inhibition of aromatase activity respectively.

Then, as envisioned, the inventors made several compositions (compositions-111 to 195) by combining one testosterone booster ingredient selected from the extracts, fractions and pure compounds derived from *Punica granatum*,

*Cinnamomum zeylanicum, Nigella sativa, Brassica nigra* and *Mangifera indica* and one aromatase inhibitor ingredient selected from the extracts, fractions and pure compounds derived from *Allium cepa, Tamarindus indica* and *Cinnamomum tamala* at different ratios and the compositions so obtained were tested for their testosterone boosting and aromatase inhibition activities to evaluate their ability to exhibit synergistic activity.

Interestingly, *Punica granatum* rind extract exhibited synergism when combined with a plant extract derived from *Allium cepa, Tamarindus indica* or *Cinnamomum tamala* as illustrated hereinafter for a few selected compositions of these ingredients. For example, *Punica granatum* rind 70% ethanol extract (PG-4) and *Cinnamomum tamala* leaf 90% ethanol extract (C.T-1) showed 5.31% and 3.66% increase in testosterone levels respectively at a treatment concentration of 0.1 mg/mL. The composition-123 (C-123) containing these two extracts at 1:1 ratio showed significantly better efficacy with 19.73% improvement in testosterone levels at 0.2 mg/mL concentration, which is better than the additive effect (5.31%+3.66%=8.97%) from the above two ingredients, suggesting synergistic effect between *Punica granatum* rind 70% ethanol extract (P.G-4) and *Cinnamomum tamala* leaf 90% ethanol extract (C.T-1). These two ingredients also showed synergism when combined at other ratios, such as 3:1, 2:1, 1:2 and 1:3 as shown by the improved testosterone levels exhibited by the compositions-121, 122, 124 and 125 respectively. These compositions showed 24.05%, 19.23%, 17.48% and 20.68% improvements in testosterone levels, which are better than the corresponding additive effects 7.02%, 7.12%, 7.56% and 13.24% respectively as summarized in Table 9. The synergistic efficacy was also observed between other solvent extracts of *Punica granatum* rind and *Cinnamomum tamala* leaf. The compositions-127, 128 and 129 containing water extract of *Punica granatum* rind (P.G-6) and water extract of *Cinnamomum tamala* leaf (C.T-4) at 2:1, 1:1 and 1:2 ratios respectively showed 30.84%, 33.18% and 32.10% increase in testosterone concentration, which are better than the corresponding additive effects at 13.7%, 19.91% and 16.42% respectively as summarized in Table 9.

Similar effects were also observed, when *Punica granatum* rind extracts were combined with other aromatase inhibiting extracts derived from *Allium cepa* or *Tamarindus indica* as exemplified by the synergistic testosterone boosting effects observed for the compositions-112, 113 and 114, which contain *Punica granatum* rind 70% ethanol extract (P.G-4) and *Allium cepa* water extract (A.C-1) at ratios 2:1, 1:1 and 1:2 respectively; and also by the compositions-117, 118 and 119, which contain *Punica granatum* rind 70% ethanol extract (P.G-4) and *Tamarindus indica* seed 90% ethanol extract (T.I-2) at ratios 2:1, 1:1 and 1:2 respectively. The testosterone improvements observed for these compositions was significantly above the additive effects calculated from the efficacy shown by the corresponding individual ingredients of the composition as summarized in Table-9.

Interestingly, the above compositions (compositions-111 to 135) containing a testosterone boosting extract derived from *Punica granatum* rind in combination with an aromatase inhibiting extract derived from *Allium cepa, Tamarindus indica* or *Cinnamomum tamala* also showed synergistic inhibition of aromatase as disclosed hereinafter for a few selected compositions. For example, *Punica granatum* rind 70% ethanol extract (P.G-4) and *Cinnamomum tamala* leaf 90% ethanol extract (C.T-1) showed 3.19% and 0.82% inhibition of aromatase respectively at a treatment concentration of 0.5 mg/mL. The composition-123 (C-123) containing these two extracts at 1:1 ratio showed significantly better efficacy with 16.50% inhibition of aromatase at 1 mg/mL concentration, which is better than the additive effect (3.19%+0.82%=4.01%) from the above two ingredients, suggesting synergistic inhibition of aromatase by *Punica granatum* rind 70% ethanol extract (P.G-4) and *Cinnamomum tamala* leaf 90% ethanol extract (C.T-1). These two ingredients also showed synergism when combined at other ratios, such as 3:1, 2:1, 1:2 and 1:3 as shown by the better aromatase inhibition exhibited by the compositions-121, 122, 124 and 125 respectively. These compositions showed 10.41%, 18.93%, 22.71% and 11.14% inhibition of aromatase, which are better than the corresponding additive effects 5.19%, 6.17%, 5.32% and 2.60% respectively as summarized in Table 14. The synergistic efficacy was also observed between other solvent extracts of *Punica granatum* rind and *Cinnamomum tamala* leaf. The compositions-127, 128 and 129 containing water extract of *Punica granatum* rind (P.G-6) and water extract of *Cinnamomum tamala* leaf (C.T-4) at 2:1, 1:1 and 1:2 ratios respectively showed 32.25%, 28.46% and 27.8% inhibition of aromatase, which are better than the corresponding additive effects at 20.03%, 20.39% and 20.76% respectively as summarized in Table 14. The compositions-132, 133 and 134 containing 70% ethanol extract of *Punica granatum* rind (P.G-4) and 60% methanol extract of *Cinnamomum tamala* leaf (C.T-3) at 2:1, 1:1 and 1:2 ratios respectively also showed improved efficacy better than additive effect in inhibiting aromatase activity as summarized in Table 14.

The synergistic data for the compositions (compositions-136 to 150) containing a testosterone boosting extract derived from *Cinnamomum zeylanicum* in combination with an aromatase inhibiting extract derived from *Allium cepa, Tamarindus indica* or *Cinnamomum tamala* is summarized in Table 10 (testosterone boosting) and Table 15 (Aromatase inhibition). Similarly, the synergistic data for the compositions (compositions-151 to 165) containing a testosterone boosting extract derived from *Nigella sativa* in combination with an aromatase inhibiting extract derived from *Allium cepa, Tamarindus indica* or *Cinnamomum tamala* is summarized in Table 11 (testosterone boosting) and Table 16 (Aromatase inhibition). The synergistic data for the compositions (compositions-166 to 180) containing a testosterone boosting extract derived from *Brassica nigra* in combination with an aromatase inhibiting extract derived from *Allium cepa, Tamarindus indica* or *Cinnamomum tamala* is summarized in Table 12 (testosterone boosting) and Table 17 (Aromatase inhibition). Finally, the synergistic data for the compositions (compositions-181 to 195) containing a testosterone boosting extract derived from *Manjifera indica* in combination with an aromatase inhibiting extract derived from *Allium cepa, Tamarindus indica* or *Cinnamomum tamala* is summarized in Table 13 (testosterone boosting) and Table 18 (Aromatase inhibition).

A few selected compositions of the current invention containing *Punica granatum* rind 70% ethanol extract (PG-4) in combination with 90% ethanol extract of *Brassica nigra* (B.N-2) [Composition-196 (C-196)]; with 90% ethanol extract of *Cinnamomum zeylanicum* (C.Z-2) [Composition-197 (C-197)]; with water extract of *Nigella sativa* (N.S-1) [Composition-198 (C-198)]; or with 90% ethanol extract of *Cinnamomum tamala* (C.T-1) [Composition-199 (C-199)], wherein each composition further contain excipients, were then evaluated for their efficacy in vivo to increase testosterone levels in male rats. Briefly, healthy male Sprague Dawley rats were acclimatized and randomized into eight groups (G1 to G8). The treatment group animals were supplemented with C-196 (G2; 100 mg/kg), C-196 (G3; 200 mg/kg; p.o.), C-197 (G4; 100 mg/kg), C197 (C5; 200 mg/kg; p.o.), C-198 (G6; 100 mg/kg), C-198 (G7; 200 mg/kg; p.o.) or C-199 (G8; 200 mg/kg; p.o.) once daily for 6 weeks in suitable vehicle. The control group (G1) animals were supplemented with vehicle only. On day:43˘, blood sample was collected from all the animals, serum was separated and analyzed for testosterone levels by E LISA. On the day of sacrifice, i.e., on day 43, animals were euthanized and caudal epididymides along with vas deferens (both side) were dissected out and the semen sample squeezed out into Dulbecco˘ s Phosphate Buffered Saline for analysis of sperm count.

Figure 2:
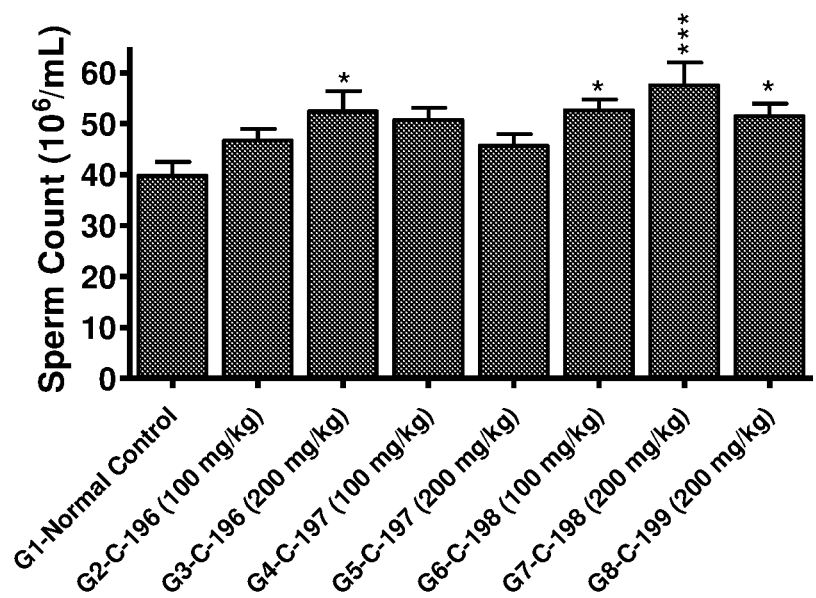
FIG. 2: The bar chart represents sperm count on day 43 in control group (G1) and treatment groups, G2 to G8 and each bar represent mean ± S.E.M, n=7. Data was analyzed using ANOVA followed by Dunnett's post-hoc test. *$P<0.05$, ***$P<0.001$ vs Normal control.

All the treatment groups displayed significant increase in testosterone levels in serum samples collected on day 43 [G2 (17.38%), G3 (33.79%), G4 (8.11%), G5 (77.38%), G6 (36.41%), G7 (5.83%) and G8 (41.70%)] when compared to the control group. The testosterone levels exhibited by different treatment groups are summarized in Table 19 and depicted in FIG. 1. Similarly, all the treatment groups showed improved sperm count when compared to the control group. However, the animals of groups, G3, G6, G7 and G8 treated with C-196 [200 mg/kg), C-198 (100 mg/kg), C198 (200 mg/kg) and C-199 (200 mg/kg) respectively displayed statistically significant increases in sperm count as summarized in Table 20 and depicted in FIG. 2. These results suggest increased androgenic activity in the animals treated with inventive compositions.

Therefore, one important embodiment of the present invention is to provide synergistic herbal compositions comprising at least two ingredients selected from the extract(s), fraction(s), active compound(s) and phytochemicals or mixtures thereof derived from the plant parts of *Punica granatum, Cinnamomum zeylanicum, Nigella sativa, Brassica nigra* and *Mangifera indica* for improving concentrations of testosterone and alleviating the symptoms/conditions associated with the low levels of testosterone in humans, which include but not limited to loss of libido, erectile dysfunction, low sperm count, abdominal obesity, decreased muscle mass and strength, decreased bone density, decreased motivation, decreased memory and concentration; and for increasing energy, the muscle strength and muscle mass. In the other important embodiment the present invention provides synergistic herbal compositions comprising at least one testosterone booster ingredient selected from the extract(s), fraction(s), active compound(s) and phytochemicals or mixtures thereof derived from the plant parts of *Punica granatum, Cinnamomum zeylanicum, Nigella sativa, Brassica nigra* and *Mangifera indica* and at least one aromatase inhibitor ingredient selected from the extract(s), fraction(s), active compound(s) and phytochemicals or mixtures thereof derived from the plant parts of *Allium cepa, Tamarindus indica* and *Cinnamomum tamala* for improving concentrations of testosterone and alleviating the symptoms/conditions associated with the low levels of testosterone in humans, which include but not limited to loss of libido, erectile dysfunction, low sperm count, abdominal obesity, decreased muscle mass and strength, decreased bone density, decreased motivation, and decreased memory and concentration; and for increasing energy, the muscle strength and muscle mass.

In another embodiment, the invention provides the composition(s) as described above for increasing the testosterone levels in a human subject, wherein solvents used for preparing the extracts can be selected from but not limited to C1-C5 alcohols, like ethanol, methanol, n-propanol, isopropyl alcohol; ketones like acetone, methylisobutyl ketone, chlorinated solvents like methylene dichloride and chloroform, water and mixtures thereof; C1-C7 hydrocarbons such as hexane; esters like ethyl acetate and the like and mixtures thereof.

In another embodiment, the invention provides synergistic composition(s) as described above for increasing the testosterone levels in a male subject, wherein the synergistic compositions contain optionally at least one additional component selected from the group consisting of biological agent(s); pharmaceutically acceptable active ingredients, vitamins, minerals; pharmaceutically or nutraceutically or dietically acceptable, excipients, carriers or diluents.

In another embodiment, the invention provides the composition(s) as described above for increasing testosterone levels in a human subject, wherein the plant parts used for preparing the extracts can be selected from leaves, stems, tender stems, tender twigs, aerial parts, whole fruit, fruit rind, seed, bulb, flower heads, root, bark, hardwood or whole plant or mixtures thereof.

In the other embodiment the present invention provides composition(s) as described above for increasing the concentration of testosterone in a human subject, where in the extracts or fractions are standardized to at least one phytochemical reference marker compound or biological active marker in the extract or fraction.

In other embodiment the present invention provides use of synergistic herbal compositions comprising extracts or fractions derived from at least two herbs selected from *Punica granatum, Cinnamomum zeylanicum, Nigella sativa, Brassica nigra* and *Mangifera indica* to increase testosterone levels, treat sexual dysfunction, improve sexual function, improve energy, enhance feelings of well-being and to increase muscle strength and muscle mass in humans.

In other embodiment the present invention provides use of synergistic herbal compositions comprising at least one extract or fraction derived from a testosterone booster herb selected from *Punica granatum, Cinnamomum zeylanicum, Nigella sativa, Brassica nigra* and *Mangifera indica* and at least one extract or fraction derived from an aromatase inhibitor herb selected from *Allium cepa, Tamarindus indica* or *Cinnamomum tamala* to increase testosterone levels, treat sexual dysfunction, improve sexual function, improve energy, enhance feelings of well-being and to increase muscle strength and muscle mass in males.

In a further embodiment the present invention provides methods of improving testosterone levels, for increasing the muscle strength and muscle mass, and to treat/alleviate symptoms/conditions associated with low levels of testosterone, which include but not limited to loss of libido, erectile dysfunction, low sperm count, abdominal obesity, decreased muscle mass and strength, decreased bone density, decreased motivation, and decreased memory and concentration in a human subject, wherein the method comprises supplementing the human subject with an effective dose of a composition comprising at least two ingredients selected from the extracts, fractions and pure compounds derived from *Punica granatum, Cinnamomum zeylanicum, Nigella sativa, Brassica nigra* or *Mangifera indica*. In a further embodiment the present invention provides methods of improving testosterone levels, for increasing the muscle strength and muscle mass, and to treat/alleviate symptoms/conditions associated with low levels of testosterone, which include but not limited to loss of libido, erectile dysfunction, low sperm count, abdominal obesity, decreased muscle mass and strength, decreased bone density, decreased motivation, and decreased memory and concentration in a male human subject, wherein the method comprises supplementing with an effective dose of a composition comprising at least one extract or fraction derived from a testosterone booster herb selected from *Punica granatum, Cinnamomum zeylanicum, Nigella sativa, Brassica nigra* and *Mangifera indica* and at least one extract or fraction derived from an aromatase inhibitor herb selected from *Allium cepa, Tamarindus indica* or *Cinnamomum tamala*.

In another exemplary embodiment the inventive compositions comprising at least two ingredients selected from the extracts, fractions and pure compounds derived from *Punica granatum, Cinnamomum zeylanicum, Nigella sativa, Brassica nigra* or *Mangifera indica* can further be combined optionally with biological agents and one or more pharmaceutically or dietetically acceptable excipients, carriers and diluents, which include but not limited to glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants and wax.

In another exemplary embodiment the inventive compositions comprising at least one testosterone booster ingredient selected from the extracts, fractions and pure compounds derived from *Punica granatum, Cinnamomum zeylanicum, Nigella sativa, Brassica nigra* and *Mangifera indica* and at least one aromatase inhibitor ingredient selected from the extracts, fractions and pure compounds derived from *Allium cepa, Tamarindus indica* or *Cinnamomum tamala* can further be combined optionally with one or more pharmaceutically or dietetically acceptable excipients, carriers and diluents, which include but not limited to glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable of Is, white soft paraffin, paraffin, flavorants, colourants and wax.

In another embodiment, the extracts or fractions or composition(s) of the present invention may be formulated into a dosage form selected from dry powder form, liquid form, beverage, food product, dietary supplement or any suitable form such as tablet, a capsule or a soft chewable or gummy bear.

In another embodiment of the invention, the composition(s) as disclosed above can be formulated into nutritional/dietary supplements that can be contemplated/made into the dosage form of healthy foods, or food for specified health uses such as sol id food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In yet another embodiment, the present invention provides a synergistic herbal composition comprising at least two ingredients selected from the extract(s), fraction(s), active compound(s) and phytochemicals or mixtures thereof derived from the plant parts of *Punica granatum, Cinnamomum zeylanicum Nigella sativa, Brassica nigra* and *Mangifera indica*, where in the weight of the first ingredient varies in the range of 10%-90% and the weight of the second ingredient varies in the range of 90%-10% in the composition.

In yet another embodiment, the present invention provides a synergistic herbal composition comprising at least one testosterone booster ingredient selected from the extract(s), fraction(s), active compound(s) and phytochemicals or mixtures thereof derived from the plant parts of *Punica granatum, Cinnamomum zeylanicum Nigella sativa, Brassica nigra* and *Mangifera indica* and at least one aromatase inhibitor ingredient selected from the extract(s), fraction(s), active compound(s) and phytochemicals or mixtures thereof derived from the plant parts of *Allium cepa, Tamarindus indica* or *Cinnamomum tamala*, wherein the weight of testosterone booster ingredient varies in the range of 10%-90% in the composition and the weight of aromatase inhibiter ingredient varies in the range of 90%-10% in the composition.

In a further embodiment, the invention provides use of a composition comprising at least two ingredients selected from the extract(s), fraction(s), active compound(s) and phytochemicals or mixtures thereof derived from the plant parts of *Punica granatum, Cinnamomum zeylanicum, Nigella sativa, Brassica nigra* and *Mangifera indica* and optionally containing pharmaceutically or nutraceutically or dietetically acceptable carriers/excipients for increasing the testosterone levels, treating/alleviating at least one symptom/condition associated with low levels of testosterone and/or for increasing the muscle strength and muscle mass.

In a further embodiment, the invention provides use of a composition comprising at least one testosterone booster ingredient selected from the extract(s), fraction(s), active compound(s) and phytochemicals or mixtures thereof derived from the plant parts of *Punica granatum Cinnamomum zeylanicum Nigella sativa, Brassica nigra* and *Mangifera indica* and at least one aromatase inhibitor ingredient selected from the extract(s), fraction(s), active compound(s) and phytochemicals or mixtures thereof derived from the plant parts of *Allium cepa, Tamarindus indica* or *Cinnamomum tamala* and optionally containing pharmaceutically or nutraceutically or dietetically acceptable carriers/excipients for increasing the testosterone levels, treating/alleviating at least one symptom/condition associated with low levels of testosterone and/or for increasing the muscle strength and muscle mass.

In another embodiment the composition(s) of the present invention can be delivered in the form of controlled release tablets, using controlled release polymer-based coatings by the techniques including nanotechnology, microencapsulation, colloidal carrier systems and other drug delivery systems for obtaining the desired therapeutic benefit.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

EXAMPLES

Example 1: Preparation of *Punica granatum* Extracts

*Punica granatum* fruit rind (100 g) was pulverized and the powder was charged into a lab extractor and extracted with ethanol (700 mL) at rt for 1 h. The extract was filtered and the spent raw material was re-extracted twice with ethanol (2×500 mL) under similar conditions. The combined extract was filtered and concentrated under vacuum to obtain a residue of ethanol extract (P.G-1; 32 g).

The 90% aqueous ethanol extract (P.G-2; 34 g), 80% aqueous ethanol extract (P.G-3; 41 g), 70% aqueous ethanol extract (P.G-4; 50 g), 50% aqueous ethanol extract (P.G-5; 38 g), water extract (P.G-6; 32 g) and methanol extract (P.G-7; 26 g) were obtained from 100 g raw material by adopting similar procedure using 90% aqueous ethanol, 80% aqueous ethanol, 70% aqueous ethanol, 50% aqueous ethanol, water and methanol as extraction solvents respectively.

These extracts were standardized to punicalagin by analytical HPLC method and the results were summarized in Table 1.

TABLE 1

Details of Punica granatum extracts

| S. No. | Extract code | Solvent for extraction | Weight of the product | Punicalagin (HPLC) |
|---|---|---|---|---|
| 1 | P.G-1 | Ethanol | 32 g | 18.73% |
| 2 | P.G-2 | 90% ethanol | 34 g | 17.36% |
| 3 | P.G-3 | 80% ethanol | 41 g | 15.76% |
| 4 | P.G-4 | 70% ethanol | 50 g | 17.66% |
| 5 | P.G-5 | 50% ethanol | 38 g | 16.03% |
| 6 | P.G-6 | water | 32 g | 6.03% |

Example 2: Preparation of *Cinnamomum zeylanicum* Extracts

*Cinnamomum zeylanicum* bark (100 g) were pulverized and the powder was charged into a lab extractor and extracted with ethanol (700 mL) at rt for 1 h. The extract was filtered and the spent raw material was re-extracted twice with ethanol (2×500 mL) under similar conditions. The combined ethanol extract was filtered and concentrated under vacuum to obtain the product as a thick paste (C.Z-1; 7.0 g).

The 90% aqueous ethanol extract (C.Z-2; 7.5 g), 50% aqueous ethanol extract (C.Z-3; 9.6 g), water extract (C.Z-4; 5.3 g) and methanol extract (C.Z-5; 9 g) were obtained by adopting similar procedure using 90% aqueous ethanol, 50% aqueous ethanol, water and methanol as extraction solvents respectively. The 90% aqueous ethanol extract (C.Z-2) was standardized to proanthocynidines by UV and the value is 25%.

Example 3: Preparation of *Nigella sativa* Extracts

*Nigella sativa* seed/fruits (100 g) were pulverized and the powder was charged into a lab extractor and extracted with water (700 mL) at rt for 1 h. The extract was filtered and the spent raw material was re-extracted twice with water (2×500 mL) under similar conditions. The combined water extract was filtered and concentrated under vacuum to obtain the product as a thick paste (N.S-1; 6.0 g). The extract was standardized to polyphenols and flavonoids by UV and the values are 4.54% and 3.24% respectively.

The 50% aqueous ethanol extract (N.S-2; 10.1 g), ethanol extract (N.S-3; 9.5 g) and methanol extract (N.S-4; 13 g) were obtained by adopting similar procedure using 50% aqueous ethanol, ethanol and methanol as extraction solvents respectively.

Example 4: Preparation of *Brassica nigra* Extracts

*Brassica nigra* seeds (100 g) were pulverized and the powder was charged into a lab extractor and extracted with ethanol (700 mL) at rt for 1 h. The extract was filtered and the spent raw material was re-extracted twice with ethanol (2×500 mL) under similar conditions. The combined ethanol extract was filtered and concentrated under vacuum to obtain the product as a thick paste (B.N-1; 6.0 g). The 90% aqueous ethanol extract (B.N-2; 6.5 g), 50% aqueous ethanol extract (B.N-3; 12.4 g), water extract (B.N-4; 21.3 g) and methanol extract (B.N-5; 10.5 g) were obtained by adopting similar procedure using 90% aqueous ethanol, 50% aqueous ethanol, water and methanol as extraction solvents respectively. The 90% aqueous ethanol extract (B.N-2) was standardized to polyphenols and flavonoids by UV and the values are 4.44% and 6.06% respectively.

Example 5: Preparation of *Mangifera indica* Extracts

*Mangifera indica* stem bark (100 g) was pulverized and the powder was charged into a lab extractor and extracted with 50% aqueous ethanol (700 mL) at rt for 1 h. The extract was filtered and the spent raw material was re-extracted twice with 50% aqueous ethanol (2×500 mL) under similar conditions. The combined extract was filtered and concentrated under vacuum to obtain a dark brown color residue of 50% aqueous ethanol extract (M.I-1; 17.2 g).

The ethanol extract (M.I-2; 9.5 g) and water extract (M.I-3; 10 g) were obtained by adopting similar procedure using ethanol and water as extraction solvents respectively.

*Mangifera indica* leaf extract is prepared by using 1:1 ethanol/water as described above gave 50% aqueous ethanol extract (M.I-4, 15 g) as pale brown color solid. These extracts were standardized to Mangiferin by analytical HPLC method and the values for M.I-1, M.I-2, N.I-3 & M.I-4 are 17.42%, 22.23%, 6.53% and 5.89% respectively.

Example 6: Preparation of Compositions Containing Extracts of *Punica granatum* and *Cinnamomum zeylanicum*

Composition-1 (C-1): The composition-1 was prepared by combining *Punica granatum* ethanol extract (P.G-1) and *Cinnamomum zeylanicum* ethanol extract (C.Z-1) in the ratio of 1:3.

Composition-2 (C-2): The composition-2 was prepared by combining *Punica granatum* ethanol extract (P.G-1) and *Cinnamomum zeylanicum* ethanol extract (C.Z-1) in the ratio of 1:2.

Composition-3 (C-3): The composition-3 was prepared by combining *Punica granatum* ethanol extract (P.G-1) and *Cinnamomum zeylanicum* ethanol extract (C.Z-1) in the ratio of 1:1.

Composition-4 (C-4): The composition-4 was prepared by combining *Punica granatum* ethanol extract (P.G-1) and *Cinnamomum zeylanicum* ethanol extract (C.Z-1) in the ratio of 2:1.

Composition-5 (C-5): The composition-5 was prepared by combining *Punica granatum* ethanol extract (P.G-1) and *Cinnamomum zeylanicum* ethanol extract (C.Z-1) in the ratio of 3:1.

Composition-6 (C-6): The composition-6 was prepared by combining *Punica granatum* 70% aqueous ethanol extract (P.G-4) and *Cinnamomum zeylanicum* 90% aqueous ethanol extract (C.Z-2) in the ratio of 3:1.

Composition-7 (C-7): The composition-7 was prepared by combining *Punica granatum* 70% aqueous ethanol extract (P.G-4) and *Cinnamomum zeylanicum* 90% aqueous ethanol extract (C.Z-2) in the ratio of 2:1.

Composition-8 (C-8): The composition-8 was prepared by combining *Punica granatum* 70% aqueous ethanol extract (P.G-4) and *Cinnamomum zeylanicum* 90% aqueous ethanol extract (C.Z-2) in the ratio of 1:1.

Composition-9 (C-9): The composition-9 was prepared by combining *Punica granatum* 70% aqueous ethanol extract (P.G-4) and *Cinnamomum zeylanicum* 90% aqueous ethanol extract (C.Z-2) in the ratio of 1:2.

Composition-10 (C-10): The composition-10 was prepared by combining *Punica granatum* 70% aqueous ethanol extract (P.G-4) and *Cinnamomum zeylanicum* 90% aqueous ethanol extract (C.Z-2) in the ratio of 1:3.

Composition-11 (C-11): The composition-11 was prepared by combining *Punica granatum* ethanol extract (P.G-1) and *Cinnamomum zeylanicum* 90% aqueous ethanol extract (C.Z-2) in the ratio of 3:1.

Composition-12 (C-12): The composition-12 was prepared by combining *Punica granatum* ethanol extract (P.G-1) and *Cinnamomum zeylanicum* 90% aqueous ethanol extract (C.Z-2) in the ratio of 2:1.

Composition-13 (C-13): The composition-13 was prepared by combining *Punica granatum* ethanol extract (P.G-1) and *Cinnamomum zeylanicum* 90% aqueous ethanol extract (C.Z-2) in the ratio of 1:1.

Composition-14 (C-14): The composition-14 was prepared by combining *Punica granatum* ethanol extract (P.G-1) and *Cinnamomum zeylanicum* 90% aqueous ethanol extract (C.Z-2) in the ratio of 1:2.

Composition-15 (C-15): The composition-15 was prepared by combining *Punica granatum* ethanol extract (P.G-1) and *Cinnamomum zeylanicum* 90% aqueous ethanol extract (C.Z-2) in the ratio of 1:3.

Composition-16 (C-16): The composition-16 was prepared by combining *Punica granatum* water extract (P.G-6) and *Cinnamomum zeylanicum* water extract (C.Z-4) in the ratio of 3:1.

Composition-17 (C-17): The composition-17 was prepared by combining *Punica granatum* water extract (P.G-6) and *Cinnamomum zeylanicum* water extract (C.Z-4) in the ratio of 2:1.

Composition-18 (C-18): The composition-18 was prepared by combining *Punica granatum* water extract (P.G-6) and *Cinnamomum zeylanicum* water extract (C.Z-4) in the ratio of 1:1.

Composition-19 (C-19): The composition-19 was prepared by combining *Punica granatum* water extract (P.G-6) and *Cinnamomum zeylanicum* water extract (C.Z-4) in the ratio of 1:2.

Composition-20 (C-20): The composition-20 was prepared by combining *Punica granatum* water extract (P.G-6) and *Cinnamomum zeylanicum* water extract (C.Z-4) in the ratio of 1:3.

Example 7: Preparation of Compositions Containing Extracts of *Punica granatum* and *Nigella sativa*

Composition-21 (C-21): The composition-21 was prepared by combining *Punica granatum* ethanol extract (P.G-1) and *Nigella sativa* water extract (N.S-1) in the ratio of 1:3.

Composition-22 (C-22): The composition-22 was prepared by combining *Punica granatum* ethanol extract (P.G-1) and *Nigella sativa* water extract (N.S-1) in the ratio of 1:2.

Composition-23 (C-23): The composition-23 was prepared by combining *Punica granatum* ethanol extract (P.G-1) and *Nigella sativa* water extract (N.S-1) in the ratio of 1:1.

Composition-24 (C-24): The composition-24 was prepared by combining *Punica granatum* ethanol extract (P.G-1) and *Nigella sativa* water extract (N.S-1) in the ratio of 2:1.

Composition-25 (C-25): The composition-25 was prepared by combining *Punica granatum* ethanol extract (P.G-1) and *Nigella sativa* water extract (N.S-1) in the ratio of 3:1.

Composition-26 (C-26): The composition-26 was prepared by combining *Punica granatum* 70% aqueous ethanol extract (P.G-4) and *Nigella sativa* water extract (N.S-1) in the ratio of 3:1.

Composition-27 (C-27): The composition-27 was prepared by combining *Punica granatum* 70% aqueous ethanol extract (P.G-4) and *Nigella sativa* water extract (N.S-1) in the ratio of 2:1.

Composition-28 (C-28): The composition-28 was prepared by combining *Punica granatum* 70% aqueous ethanol extract (P.G-4) and *Nigella sativa* water extract (N.S-1) in the ratio of 1:1.

Composition-29 (C-29): The composition-29 was prepared by combining *Punica granatum* 70% aqueous ethanol extract (P.G-4) and *Nigella sativa* water extract (N.S-1) in the ratio of 1:2.

Composition-30 (C-30): The composition-30 was prepared by combining *Punica granatum* 70% aqueous ethanol extract (P.G-4) and *Nigella sativa* water extract (N.S-1) in the ratio of 1:3.

Composition-31 (C-31): The composition-31 was prepared by combining *Punica granatum* water extract (P.G-6) and *Nigella sativa* water extract (N.S-1) in the ratio of 3:1.

Composition-32 (C-32): The composition-32 was prepared by combining *Punica granatum* water extract (P.G-6) and *Nigella sativa* water extract (N.S-1) in the ratio of 2:1.

Composition-33 (C-33): The composition-33 was prepared by combining *Punica granatum* water extract (P.G-6) and *Nigella sativa* water extract (N.S-1) in the ratio of 1:1.

Composition-34 (C-34): The composition-34 was prepared by combining *Punica granatum* water extract (P.G-6) and *Nigella sativa* water extract (N.S-1) in the ratio of 1:2.

Composition-35 (C-35): The composition-35 was prepared by combining *Punica granatum* water extract (P.G-6) and *Nigella sativa* water extract (N.S-1) in the ratio of 1:3.

Composition-35A (C-35A): The composition-35A was prepared by combining *Punica granatum* 70% aqueous ethanol extract (P.G-4) and *Nigella sativa* 50% aqueous ethanol extract (N.S-2) in the ratio of 2:1.

Composition-35B (C-35B): The composition-35B was prepared by combining *Punica granatum* 70% aqueous ethanol extract (P.G-4) and *Nigella sativa* 50% aqueous ethanol extract (N.S-2) in the ratio of 1:1.

Composition-35C (C-35C): The composition-35C was prepared by combining *Punica granatum* 70% aqueous ethanol extract (P.G-4) and *Nigella sativa* 50% aqueous ethanol extract (N.S-2) in the ratio of 1:2.

Example 8: Preparation of Compositions Containing Extracts of *Punica granatum* and *Brassica nigra*

Composition-36 (C-36): The composition-36 was prepared by combining *Punica granatum* ethanol extract (P.G-1) and *Brassica nigra* ethanol extract (B.N-1) in the ratio of 1:3.

Composition-37 (C-37): The composition-37 was prepared by combining *Punica granatum* ethanol extract (P.G-1) and *Brassica nigra* ethanol extract (B.N-1) in the ratio of 1:2.

Composition-38 (C-38): The composition-38 was prepared by combining *Punica granatum* ethanol extract (P.G-1) and *Brassica nigra* ethanol extract (B.N-1) in the ratio of 1:1.

Composition-39 (C-39): The composition-39 was prepared by combining *Punica granatum* ethanol extract (P.G-1) and *Brassica nigra* ethanol extract (B.N-1) in the ratio of 2:1.

Composition-40 (C-40): The composition-40 was prepared by combining *Punica granatum* ethanol extract (P.G-1) and *Brassica nigra* ethanol extract (B.N-1) in the ratio of 3:1.

Composition-41 (C-41): The composition-41 was prepared by combining *Punica granatum* 70% aqueous ethanol extract (P.G-4) and *Brassica nigra* 90% aqueous ethanol extract (B.N-2) in the ratio of 3:1.

Composition-42 (C-42): The composition-42 was prepared by combining *Punica granatum* 70% aqueous ethanol extract (P.G-4) and *Brassica nigra* 90% aqueous ethanol extract (B.N-2) in the ratio of 2:1.

Composition-43 (C-43): The composition-43 was prepared by combining *Punica granatum* 70% aqueous ethanol extract (P.G-4) and *Brassica nigra* 90% aqueous ethanol extract (B.N-2) in the ratio of 1:1.

Composition-44 (C-44): The composition-44 was prepared by combining *Punica granatum* 70% aqueous ethanol extract (P.G-4) and *Brassica nigra* 90% aqueous ethanol extract (B.N-2) in the ratio of 1:2.

Composition-45 (C-45): The composition-45 was prepared by combining *Punica granatum* 70% aqueous ethanol extract (P.G-4) and *Brassica nigra* 90% aqueous ethanol extract (B.N-2) in the ratio of 1:3.

Composition-46 (C-46): The composition-46 was prepared by combining *Punica granatum* water extract (P.G-6) and *Brassica nigra* water extract (B.N-4) in the ratio of 3:1.

Composition-47 (C-47): The composition-47 was prepared by combining *Punica granatum* water extract (P.G-6) and *Brassica nigra* water extract (B.N-4) in the ratio of 2:1.

Composition-48 (C-48): The composition-48 was prepared by combining *Punica granatum* water extract (P.G-6) and *Brassica nigra* water extract (B.N-4) in the ratio of 1:1.

Composition-49 (C-49): The composition-49 was prepared by combining *Punica granatum* water extract (P.G-6) and *Brassica nigra* water extract (B.N-4) in the ratio of 1:2.

Composition-50 (C-50): The composition-50 was prepared by combining *Punica granatum* water extract (P.G-6) and *Brassica nigra* water extract (B.N-4) in the ratio of 1:3.

Composition-51 (C-51): The composition-51 was prepared by combining *Punica granatum* methanol extract (P.G-7) and *Brassica nigra* water extract (B.N-4) in the ratio of 3:1.

Composition-52 (C-52): The composition-52 was prepared by combining *Punica granatum* methanol extract (P.G-7) and *Brassica nigra* water extract (B.N-4) in the ratio of 2:1.

Composition-53 (C-53): The composition-53 was prepared by combining *Punica granatum* methanol extract (P.G-7) and *Brassica nigra* water extract (B.N-4) in the ratio of 1:1.

Composition-54 (C-54): The composition-54 was prepared by combining *Punica granatum* methanol extract (P.G-7) and *Brassica nigra* water extract (B.N-4) in the ratio of 1:2.

Composition-55 (C-55): The composition-55 was prepared by combining *Punica granatum* methanol extract (P.G-7) and *Brassica nigra* water extract (B.N-4) in the ratio of 1:3.

Composition-56 (C-56): The composition-56 was prepared by combining *Punica granatum* 70% aqueous ethanol extract (P.G-4) and *Brassica nigra* methanol extract (B.N-5) in the ratio of 3:1.

Composition-57 (C-57): The composition-57 was prepared by combining *Punica granatum* 70% aqueous ethanol extract (P.G-4) and *Brassica nigra* methanol extract (B.N-5) in the ratio of 2:1.

Composition-58 (C-58): The composition-58 was prepared by combining *Punica granatum* 70% aqueous ethanol extract (P.G-4) and *Brassica nigra* methanol extract (B.N-5) in the ratio of 1:1.

Composition-59 (C-59): The composition-59 was prepared by combining *Punica granatum* 70% aqueous ethanol extract (P.G-4) and *Brassica nigra* methanol extract (B.N-5) in the ratio of 1:2.

Composition-60 (C-60): The composition-60 was prepared by combining *Punica granatum* 70% aqueous ethanol extract (P.G-4) and *Brassica nigra* methanol extract (B.N-5) in the ratio of 1:3.

Example 9: Preparation of Compositions Containing Extracts of *Punica granatum* and *Mangifera indica*

Composition-61 (C-61): The composition-61 was prepared by combining *Punica granatum* 70% aqueous ethanol extract (P.G-4) and *Mangifera indica* 50% aqueous ethanol extract (M.I-1) in the ratio of 3:1.

Composition-62 (C-62): The composition-62 was prepared by combining *Punica granatum* 70% aqueous ethanol extract (P.G-4) and *Mangifera indica* 50% aqueous ethanol extract (M.I-1) in the ratio of 2:1.

Composition-63 (C-63): The composition-63 was prepared by combining *Punica granatum* 70% aqueous ethanol extract (P.G-4) and *Mangifera indica* 50% aqueous ethanol extract (M.I-1) in the ratio of 1:1.

Composition-64 (C-64): The composition-64 was prepared by combining *Punica granatum* 70% aqueous ethanol extract (P.G-4) and *Mangifera indica* 50% aqueous ethanol extract (M.I-1) in the ratio of 1:2.

Composition-65 (C-65): The composition-65 was prepared by combining *Punica granatum* 70% aqueous ethanol extract (P.G-4) and *Mangifera indica* 50% aqueous ethanol extract (M.I-1) in the ratio of 1:3.

Composition-66 (C-66): The composition-66 was prepared by combining *Punica granatum* water extract (P.G-6) and *Mangifera indica* water extract (M.I-3) in the ratio of 3:1.

Composition-67 (C-67): The composition-67 was prepared by combining *Punica granatum* water extract (P.G-6) and *Mangifera indica* water extract (M.I-3) in the ratio of 2:1.

Composition-68 (C-68): The composition-68 was prepared by combining *Punica granatum* water extract (P.G-6) and *Mangifera indica* water extract (M.I-3) in the ratio of 1:1.

Composition-69 (C-69): The composition-69 was prepared by combining *Punica granatum* water extract (P.G-6) and *Mangifera indica* water extract (M.I-3) in the ratio of 1:2.

Composition-70 (C-70): The composition-70 was prepared by combining *Punica granatum* water extract (P.G-6) and *Mangifera indica* water extract (M.I-3) in the ratio of 1:3.

Composition-70A (C-70A): The composition-70A was prepared by combining *Punica granatum* 70% aqueous ethanol extract (P.G-4) and *Mangifera indica* leaf 50% aqueous ethanol extract (M.I-4) in the ratio of 2:1.

Composition-70B (C-70B): The composition-70B was prepared by combining *Punica granatum* 70% aqueous ethanol extract (P.G-4) and *Mangifera indica* leaf 50% aqueous ethanol extract (M.I-4) in the ratio of 1:2.

Example 10: Preparation of Compositions Containing Extracts of *Cinnamomum zeylanicum* Along with *Brassica nigra*, *Nigella Sativa* and *Mangifera indica*

Composition-71 (C-71): The composition-71 was prepared by combining *Cinnamomum zeylanicum* ethanol extract (C.Z-1) and *Brassica nigra* ethanol extract (B.N-1) in the ratio of 1:3.

Composition-72 (C-72): The composition-72 was prepared by combining *Cinnamomum zeylanicum* ethanol extract (C.Z-1) and *Brassica nigra* ethanol extract (B.N-1) in the ratio of 1:2.

Composition-73 (C-73): The composition-73 was prepared by combining *Cinnamomum zeylanicum* ethanol extract (C.Z-1) and *Brassica nigra* ethanol extract (B.N-1) in the ratio of 1:1.

Composition-74 (C-74): The composition-74 was prepared by combining *Cinnamomum zeylanicum* ethanol extract (C.Z-1) and *Brassica nigra* ethanol extract (B.N-1) in the ratio of 2:1.

Composition-75 (C-75): The composition-75 was prepared by combining *Cinnamomum zeylanicum* ethanol extract (C.Z-1) and *Brassica nigra* ethanol extract (B.N-1) in the ratio of 3:1.

Composition-76 (C-76): The composition-76 was prepared by combining *Cinnamomum zeylanicum* 90% aqueous ethanol extract (C.Z-2) and *Brassica nigra* 90% aqueous ethanol extract (B.N-2) in the ratio of 3:1.

Composition-77 (C-77): The composition-77 was prepared by combining *Cinnamomum zeylanicum* 90% aqueous ethanol extract (C.Z-2) and *Brassica nigra* 90% aqueous ethanol extract (B.N-2) in the ratio of 2:1.

Composition-78 (C-78): The composition-78 was prepared by combining *Cinnamomum zeylanicum* 90% aqueous ethanol extract (C.Z-2) and *Brassica nigra* 90% aqueous ethanol extract (B.N-2) in the ratio of 1:1.

Composition-79 (C-79): The composition-79 was prepared by combining *Cinnamomum zeylanicum* 90% aqueous ethanol extract (C.Z-2) and *Brassica nigra* 90% aqueous ethanol extract (B.N-2) in the ratio of 1:2.

Composition-80 (C-80): The composition-80 was prepared by combining *Cinnamomum zeylanicum* 90% aqueous ethanol extract (C.Z-2) and *Brassica nigra* 90% aqueous ethanol extract (B.N-2) in the ratio of 1:3.

Composition-81 (C-81): The composition-81 was prepared by combining *Cinnamomum zeylanicum* 90% aqueous ethanol extract (C.Z-2) and *Nigella sativa* water extract (N.S-1) in the ratio of 3:1.

Composition-82 (C-82): The composition-82 was prepared by combining *Cinnamomum zeylanicum* 90% aqueous ethanol extract (C.Z-2) and *Nigella sativa* water extract (N.S-1) in the ratio of 2:1.

Composition-83 (C-83): The composition-83 was prepared by combining *Cinnamomum zeylanicum* 90% aqueous ethanol extract (C.Z-2) and *Nigella sativa* water extract (N.S-1) in the ratio of 1:1.

Composition-84 (C-84): The composition-84 was prepared by combining *Cinnamomum zeylanicum* 90% aqueous ethanol extract (C.Z-2) and *Nigella sativa* water extract (N.S-1) in the ratio of 1:2.

Composition-85 (C-85): The composition-85 was prepared by combining *Cinnamomum zeylanicum* 90% aqueous ethanol extract (C.Z-2) and *Nigella sativa* water extract (N.S-1) in the ratio of 1:3.

Composition-86 (C-86): The composition-86 was prepared by combining *Cinnamomum zeylanicum* 90% aqueous ethanol extract (C.Z-2) and *Mangifera indica* 50% aqueous ethanol extract (M.I-1) in the ratio of 3:1.

Composition-87 (C-87): The composition-87 was prepared by combining *Cinnamomum zeylanicum* 90% aqueous ethanol extract (C.Z-2) and *Mangifera indica* 50% aqueous ethanol extract (M.I-1) in the ratio of 2:1.

Composition-88 (C-88): The composition-88 was prepared by combining *Cinnamomum zeylanicum* 90% aqueous ethanol extract (C.Z-2) and *Mangifera indica* 50% aqueous ethanol extract (M.I-1) in the ratio of 1:1.

Composition-89 (C-89): The composition-89 was prepared by combining *Cinnamomum zeylanicum* 90% aqueous ethanol extract (C.Z-2) and *Mangifera indica* 50% aqueous ethanol extract (M.I-1) in the ratio of 1:2.

Composition-90 (C-90): The composition-90 was prepared by combining *Cinnamomum zeylanicum* 90% aqueous ethanol extract (C.Z-2) and *Mangifera indica* 50% aqueous ethanol extract (M.I-1) in the ratio of 1:3.

Example 11: Preparation of Compositions Containing Extracts of *Nigella Sativa* along with *Brassica nigra* and *Mangifera indica*

Composition-91 (C-91): The composition-91 was prepared by combining *Nigella sativa* water extract (N.S-1) and *Brassica nigra* ethanol extract (B.N-1) in the ratio of 1:3.

Composition-92 (C-92): The composition-92 was prepared by combining *Nigella sativa* water extract (N.S-1) and *Brassica nigra* ethanol extract (B.N-1) in the ratio of 1:2.

Composition-93 (C-93): The composition-93 was prepared by combining *Nigella sativa* water extract (N.S-1) and *Brassica nigra* ethanol extract (B.N-1) in the ratio of 1:1.

Composition-94 (C-94): The composition-94 was prepared by combining *Nigella sativa* water extract (N.S-1) and *Brassica nigra* ethanol extract (B.N-1) in the ratio of 2:1.

Composition-95 (C-95): The composition-95 was prepared by combining *Nigella sativa* water extract (N.S-1) and *Brassica nigra* ethanol extract (B.N-1) in the ratio of 3:1.

Composition-96 (C-96): The composition-96 was prepared by combining *Nigella sativa* water extract (N.S-1) and *Brassica nigra* 90% aqueous ethanol extract (B.N-2) in the ratio of 1:3.

Composition-97 (C-97): The composition-97 was prepared by combining *Nigella sativa* water extract (N.S-1) and *Brassica nigra* 90% aqueous ethanol extract (B.N-2) in the ratio of 1:2.

Composition-98 (C-98): The composition-98 was prepared by combining *Nigella sativa* water extract (N.S-1) and *Brassica nigra* 90% aqueous ethanol extract (B.N-2) in the ratio of 1:1.

Composition-99 (C-99): The composition-99 was prepared by combining *Nigella sativa* water extract (N.S-1) and *Brassica nigra* 90% aqueous ethanol extract (B.N-2) in the ratio of 2:1.

Composition-100 (C-100): The composition-100 was prepared by combining *Nigella sativa* water extract (N.S-1) and *Brassica nigra* 90% aqueous ethanol extract (B.N-2) in the ratio of 3:1.

Composition-101 (C-101): The composition-101 was prepared by combining *Nigella sativa* water extract (N.S-1) and *Mangifera indica* 50% aqueous ethanol extract (M.I-1) in the ratio of 3:1.

Composition-102 (C-102): The composition-102 was prepared by combining *Nigella sativa* water extract (N.S-1) and *Mangifera indica* 50% aqueous ethanol extract (M.I-1) in the ratio of 2:1.

Composition-103 (C-103): The composition-103 was prepared by combining *Nigella sativa* water extract (N.S-1) and *Mangifera indica* 50% aqueous ethanol extract (M.I-1) in the ratio of 1:1.

Composition-104 (C-104): The composition-104 was prepared by combining *Nigella sativa* water extract (N.S-1) and *Mangifera indica* 50% aqueous ethanol extract (M.I-1) in the ratio of 1:2.

Composition-105 (C-105): The composition-105 was prepared by combining *Nigella sativa* water extract (N.S-1) and *Mangifera indica* 50% aqueous ethanol extract (M.I-1) in the ratio of 1:3.

Example 12: Preparation of Compositions Containing Extracts of *Brassica nigra* and *Mangifera indica*

Composition-106 (C-106): The composition-106 was prepared by combining *Brassica nigra* ethanol extract (B.N-1) and *Mangifera indica* 50% aqueous ethanol extract (M.I-1) in the ratio of 3:1.

Composition-107 (C-107): The composition-107 was prepared by combining *Brassica nigra* ethanol extract (B.N-1) and *Mangifera indica* 50% aqueous ethanol extract (M.I-1) in the ratio of 2:1.

Composition-108 (C-108): The composition-108 was prepared by combining *Brassica nigra* ethanol extract (B.N-1) and *Mangifera indica* 50% aqueous ethanol extract (M.I-1) in the ratio of 1:1.

Composition-109 (C-109): The composition-109 was prepared by combining *Brassica nigra* ethanol extract (B.N-1) and *Mangifera indica* 50% aqueous ethanol extract (M.I-1) in the ratio of 1:2.

Composition-110 (C-110): The composition-110 was prepared by combining *Brassica nigra* ethanol extract (B.N-1) and *Mangifera indica* 50% aqueous ethanol extract (M.I-1) in the ratio of 1:3.

Example 13: Preparation of *Allium cepa* Extracts

*Allium cepa* dried bulbs (100 g) were pulverized and the powder was charged into a lab extractor and extracted with water (700 mL) at rt for 1 h. The extract was filtered and the spent raw material was re-extracted twice with water (2×500 mL) under similar conditions. The combined water extract was filtered and concentrated under vacuum to obtain the product as a dark brown color powder (A.C-1; 61.0 g). The 50% aqueous ethanol extract (A.C-2; 59.2 g) and ethanol extract (A.C-3; 10.2 g) were obtained by adopting similar procedure using 50% aqueous ethanol and ethanol as extraction solvents respectively.

Similarly, after removing outer peel of *Allium cepa* bulb (425 g) was cut into small pieces, grinded and squeezed to get the juice. The juice was fine filtered, evaporated under reduced pressure and finally freeze dried to get the extract (A.C-4) as light brown color powder (40.4 g).

Example 14: Preparation of *Tamarindus indica* Extracts

*Tamarindus indica* seeds (100 g) were pulverized and the powder was charged into a lab extractor and extracted with ethanol (700 mL) at rt for 1 h. The extract was filtered and the spent raw material was re-extracted twice with ethanol (2×500 mL) under similar conditions. The combined ethanol extract was filtered and concentrated under vacuum to obtain the product as a thick paste (T.I-1; 10.0 g). The 90% aqueous ethanol extract (T.I-2; 16.4 g), 50% aqueous ethanol extract (T.I-3; 11.9 g) and water extract (T.I-4; 7.8 g) were obtained by adopting similar procedure using 90% aqueous ethanol, 50% aqueous ethanol and water as extraction solvents respectively. The 90% aqueous ethanol extract (T.I-2) was standardized to proanthocynidines by UV and the value is 94%.

Example 15: Preparation of *Cinnamomum tamala* Extracts

*Cinnamomum tamala* leaves (100 g) were pulverized and the powder was charged into a lab extractor and extracted with 90% aqueous ethanol (700 mL) at rt for 1 h. The extract was filtered and the spent raw material was re-extracted twice with 90% aqueous ethanol (2×500 mL) under similar conditions. The combined extract was filtered and concentrated under vacuum to obtain the product (C.T-1; 20.0 g). The extract (C.T-1) was standardized to proanthocynidines by UV and the value is 16%. The methanol extract (C.T-2; 19.0 g), 60% aqueous methanol extract (C.T-3; 16.5 g), and water extract (C.T-4; 15.2 g) were obtained by adopting similar procedure using methanol, 60% aqueous methanol and water as extraction solvents respectively.

Example 16: Preparation of the Compositions Containing Extracts of *Punica granatum* in Combination with *Allium cepa, Tamarindus indica* and *Cinnamomum tamala*

Composition-111 (C-111): The composition-111 was prepared by combining *Punica granatum* 70% aqueous ethanol extract (P.G-4) and *Allium cepa* water extract (A.C-1) in the ratio of 3:1.

Composition-112 (C-112): The composition-112 was prepared by combining *Punica granatum* 70% aqueous ethanol extract (P.G-4) and *Allium cepa* water extract (A.C-1) in the ratio of 2:1.

Composition-113 (C-113): The composition-113 was prepared by combining *Punica granatum* 70% aqueous ethanol extract (P.G-4) and *Allium cepa* water extract (A.C-1) in the ratio of 1:1.

Composition-114 (C-114): The composition-114 was prepared by combining *Punica granatum* 70% aqueous ethanol extract (P.G-4) and *Allium cepa* water extract (A.C-1) in the ratio of 1:2.

Composition-115 (C-115): The composition-115 was prepared by combining *Punica granatum* 70% aqueous ethanol extract (P.G-4) and *Allium cepa* water extract (A.C-1) in the ratio of 1:3.

Composition-116 (C-116): The composition-116 was prepared by combining *Punica granatum* 70% aqueous ethanol extract (P.G-4) and *Tamarindus indica* 90% aqueous ethanol extract (T.I-2) in the ratio of 3:1.

Composition-117 (C-117): The composition-117 was prepared by combining *Punica granatum* 70% aqueous ethanol extract (P.G-4) and *Tamarindus indica* 90% aqueous ethanol extract (T.I-2) in the ratio of 2:1.

Composition-118 (C-118): The composition-118 was prepared by combining *Punica granatum* 70% aqueous ethanol extract (P.G-4) and *Tamarindus indica* 90% aqueous ethanol extract (T.I-2) in the ratio of 1:1.

Composition-119 (C-119): The composition-119 was prepared by combining *Punica granatum* 70% aqueous ethanol extract (P. G-4) and *Tamarindus indica* 90% aqueous ethanol extract (T.I-2) in the ratio of 1:2.

Composition-120 (C-120): The composition-120 was prepared by combining *Punica granatum* 70% aqueous ethanol extract (P. G-4) and *Tamarindus indica* 90% aqueous ethanol extract (T.I-2) in the ratio of 1:3.

Composition-121 (C-121): The composition-121 was prepared by combining *Punica granatum* 70% aqueous ethanol extract (P.G-4) and *Cinnamomum tamala* 90% aqueous ethanol extract (C.T-1) in the ratio of 3:1.

Composition-122 (C-122): The composition-122 was prepared by combining *Punica granatum* 70% aqueous ethanol extract (P.G-4) and *Cinnamomum tamala* 90% aqueous ethanol extract (C.T-1) in the ratio of 2:1.

Composition-123 (C-123): The composition-123 was prepared by combining *Punica granatum* 70% aqueous ethanol extract (P.G-4) and *Cinnamomum tamala* 90% aqueous ethanol extract (C.T-1) in the ratio of 1:1.

Composition-124 (C-124): The composition-124 was prepared by combining *Punica granatum* 70% aqueous ethanol extract (P.G-4) and *Cinnamomum tamala* 90% aqueous ethanol extract (C.T-1) in the ratio of 1:2.

Composition-125 (C-125): The composition-125 was prepared by combining *Punica granatum* 70% aqueous ethanol extract (P.G-4) and *Cinnamomum tamala* 90% aqueous ethanol extract (C.T-1) in the ratio of 1:3.

Composition-126 (C-126): The composition-126 was prepared by combining *Punica granatum* water extract (P. G-6) and *Cinnamomum tamala* water extract (C.T-4) in the ratio of 3:1.

Composition-127 (C-127): The composition-127 was prepared by combining *Punica granatum* water extract (P. G-6) and *Cinnamomum tamala* water extract (C.T-4) in the ratio of 2:1.

Composition-128 (C-128): The composition-128 was prepared by combining *Punica granatum* water extract (P. G-6) and *Cinnamomum tamala* water extract (C.T-4) in the ratio of 1:1.

Composition-129 (C-129): The composition-129 was prepared by combining *Punica granatum* water extract (P.G-6) and *Cinnamomum tamala* water extract (C.T-4) in the ratio of 1:2.

Composition-130 (C-130): The composition-130 was prepared by combining *Punica granatum* water extract (P.G-6) and *Cinnamomum tamala* water extract (C.T-4) in the ratio of 1:3.

Composition-131 (C-131): The composition-131 was prepared by combining *Punica granatum* 70% aqueous ethanol (P.G-4) and *Cinnamomum tamala* 60% aqueous methanol (C.T-3) in the ratio of 3:1.

Composition-132 (C-132): The composition-132 was prepared by combining *Punica granatum* 70% aqueous ethanol (P.G-4) and *Cinnamomum tamala* 60% aqueous methanol (C.T-3) in the ratio of 2:1.

Composition-133 (C-133): The composition-133 was prepared by combining *Punica granatum* 70% aqueous ethanol (P.G-4) and *Cinnamomum tamala* 60% aqueous methanol (C.T-3) in the ratio of 1:1.

Composition-134 (C-134): The composition-134 was prepared by combining *Punica granatum* 70% aqueous ethanol (P.G-4) and *Cinnamomum tamala* 60% aqueous methanol (C.T-3) in the ratio of 1:2.

Composition-135 (C-135): The composition-135 was prepared by combining *Punica granatum* 70% aqueous ethanol (P.G-4) and *Cinnamomum tamala* 60% aqueous methanol (C.T-3) in the ratio of 1:3.

Example 17: Preparation of the compositions containing extracts of *Cinnamomum* zeylanicumin combination with *Allium cepa, Tamarindus indica* and *Cinnamomum tamala*

Composition-136 (C-136): The composition-136 was prepared by combining *Cinnamomum zeylanicum* 90% aqueous ethanol extract (C.Z-2) and *Allium cepa* water extract (A.C-1) in the ratio of 3:1.

Composition-137 (C-137): The composition-137 was prepared by combining *Cinnamomum zeylanicum* 90% aqueous ethanol extract (C.Z-2) and *Allium cepa* water extract (A.C-1) in the ratio of 2:1.

Composition-138 (C-138): The composition-138 was prepared by combining *Cinnamomum zeylanicum* 90% aqueous ethanol extract (C.Z-2) and *Allium cepa* water extract (A.C-1) in the ratio of 1:1.

Composition-139 (C-139): The composition-139 was prepared by combining *Cinnamomum zeylanicum* 90% aqueous ethanol extract (C.Z-2) and *Allium cepa* water extract (A.C-1) in the ratio of 1:2.

Composition-140 (C-140): The composition-140 was prepared by combining *Cinnamomum zeylanicum* 90% aqueous ethanol extract (C.Z-2) and *Allium cepa* water extract (A.C-1) in the ratio of 1:3.

Composition-141 (C-141): The composition-141 was prepared by combining *Cinnamomum zeylanicum* 90% aqueous ethanol extract (C.Z-2) and *Tamarindus indica* 90% aqueous ethanol extract (T.I-2) in the ratio of 3:1.

Composition-142 (C-142): The composition-142 was prepared by combining *Cinnamomum zeylanicum* 90% aqueous ethanol extract (C.Z-2) and *Tamarindus indica* 90% aqueous ethanol extract (T.I-2) in the ratio of 2:1.

Composition-143 (C-143): The composition-143 was prepared by combining *Cinnamomum zeylanicum* 90% aqueous ethanol extract (C.Z-2) and *Tamarindus indica* 90% aqueous ethanol extract (T.I-2) in the ratio of 1:1.

Composition-144 (C-144): The composition-144 was prepared by combining *Cinnamomum zeylanicum* 90% aqueous ethanol extract (C.Z-2) and *Tamarindus indica* 90% aqueous ethanol extract (T.I-2) in the ratio of 1:2.

Composition-145 (C-145): The composition-145 was prepared by combining *Cinnamomum zeylanicum* 90% aqueous ethanol extract (C.Z-2) and *Tamarindus indica* 90% aqueous ethanol extract (T.I-2) in the ratio of 1:3.

Composition-146 (C-146): The composition-146 was prepared by combining *Cinnamomum zeylanicum* 90% aqueous ethanol extract (C.Z-2) and *Cinnamomum tamala* 90% aqueous ethanol extract (C.T-1) in the ratio of 3:1.

Composition-147 (C-147): The composition-147 was prepared by combining *Cinnamomum zeylanicum* 90% aqueous ethanol extract (C.Z-2) and *Cinnamomum tamala* 90% aqueous ethanol extract (C.T-1) in the ratio of 2:1.

Composition-148 (C-148): The composition-148 was prepared by combining *Cinnamomum zeylanicum* 90% aqueous ethanol extract (C.Z-2) and *Cinnamomum tamala* 90% aqueous ethanol extract (C.T-1) in the ratio of 1:1.

Composition-149 (C-149): The composition-149 was prepared by combining *Cinnamomum zeylanicum* 90% aqueous ethanol extract (C.Z-2) and *Cinnamomum tamala* 90% aqueous ethanol extract (C.T-1) in the ratio of 1:2.

Composition-150 (C-150): The composition-150 was prepared by combining *Cinnamomum zeylanicum* 90% aqueous ethanol extract (C.Z-2) and *Cinnamomum tamala* 90% aqueous ethanol extract (C.T-1) in the ratio of 1:3.

Example 18: Preparation of the Compositions Containing Extracts of *Nigella sativa* in Combination with *Allium cepa, Tamarindus Indica* and *Cinnamomum tamala*

Composition-151 (C-151): The composition-151 was prepared by combining *Nigella sativa* water extract (N.S-1) and *Allium cepa* water extract (A.C-1) in the ratio of 3:1.

Composition-152 (C-152): The composition-152 was prepared by combining *Nigella sativa* water extract (N.S-1) and *Allium cepa* water extract (A.C-1) in the ratio of 2:1.

Composition-153 (C-153): The composition-153 was prepared by combining *Nigella sativa* water extract (N.S-1) and *Allium cepa* water extract (A.C-1) in the ratio of 1:1.

Composition-154 (C-154): The composition-154 was prepared by combining *Nigella sativa* water extract (N.S-1) and *Allium cepa* water extract (A.C-1) in the ratio of 1:2.

Composition-155 (C-155): The composition-155 was prepared by combining *Nigella sativa* water extract (N.S-1) and *Allium cepa* water extract (A.C-1) in the ratio of 1:3.

Composition-155A (C-155A): The composition-155A was prepared by combining *Nigella sativa* 50% aqueous ethanol extract (N.S-2) and *Allium cepa* ethanol extract (A.C-3) in the ratio of 2:1.

Composition-155B (C-155B): The composition-1556 was prepared by combining *Nigella sativa* 50% aqueous ethanol extract (N.S-2) and *Allium cepa* ethanol extract (A.C-3) in the ratio of 1:1.

Composition-155C (C-155C): The composition-155C was prepared by combining *Nigella sativa* 50% aqueous ethanol extract (N.S-2) and *Allium cepa* ethanol extract (A.C-3) in the ratio of 1:2.

Composition-156 (C-156): The composition-156 was prepared by combining *Nigella sativa* water extract (N.S-1) and *Tamarindus indica* 90% aqueous ethanol extract (T.I-2) in the ratio of 3:1.

Composition-157 (C-157): The composition-157 was prepared by combining *Nigella sativa* water extract (N.S-1) and *Tamarindus indica* 90% aqueous ethanol extract (T.I-2) in the ratio of 2:1.

Composition-158 (C-158): The composition-158 was prepared by combining *Nigella sativa* water extract (N.S-1) and *Tamarindus indica* 90% aqueous ethanol extract (T.I-2) in the ratio of 1:1.

Composition-159 (C-159): The composition-159 was prepared by combining *Nigella sativa* water extract (N.S-1) and *Tamarindus indica* 90% aqueous ethanol extract (T.I-2) in the ratio of 1:2.

Composition-160 (C-160): The composition-160 was prepared by combining *Nigella sativa* water extract (N.S-1) and *Tamarindus indica* 90% aqueous ethanol extract (T.I-2) in the ratio of 1:3.

Composition-161 (C-161): The composition-161 was prepared by combining *Nigella sativa* water extract (N.S-1) and *Cinnamomum tamala* 90% aqueous ethanol extract (C.T-1) in the ratio of 3:1.

Composition-162 (C-162): The composition-162 was prepared by combining *Nigella sativa* water extract (N.S-1) and *Cinnamomum tamala* 90% aqueous ethanol extract (C.T-1) in the ratio of 2:1.

Composition-163 (C-163): The composition-163 was prepared by combining *Nigella sativa* water extract (N.S-1) and *Cinnamomum tamala* 90% aqueous ethanol extract (C.T-1) in the ratio of 1:1.

Composition-164 (C-164): The composition-164 was prepared by combining *Nigella sativa* water extract (N.S-1) and *Cinnamomum tamala* 90% aqueous ethanol extract (C.T-1) in the ratio of 1:2.

Composition-165 (C-165): The composition-165 was prepared by combining *Nigella sativa* water extract (N.S-1) and *Cinnamomum tamala* 90% aqueous ethanol extract (C.T-1) in the ratio of 1:3.

Example 19: Preparation of the compositions containing extracts of *Brassica nigra* in combination with *Allium cepa, Tamarindus indica* and *Cinnamomum tamala* Composition-166 (C-166): The composition-166 was prepared by combining *Brassica nigra* 90% aqueous ethanol extract (B.N-2) and *Allium cepa* water extract (A.C-1) in the ratio of 3:1.

Composition-167 (C-167): The composition-167 was prepared by combining *Brassica nigra* 90% aqueous ethanol extract (B.N-2) and *Allium cepa* water extract (A.C-1) in the ratio of 2:1.

Composition-168 (C-168): The composition-168 was prepared by combining *Brassica nigra* 90% aqueous ethanol extract (B.N-2) and *Allium cepa* water extract (A.C-1) in the ratio of 1:1.

Composition-169 (C-169): The composition-169 was prepared by combining *Brassica nigra* 90% aqueous ethanol extract (B.N-2) and *Allium cepa* water extract (A.C-1) in the ratio of 1:2.

Composition-170 (C-170): The composition-170 was prepared by combining *Brassica nigra* 90% aqueous ethanol extract (B.N-2) and *Allium cepa* water extract (A.C-1) in the ratio of 1:3.

Composition-171 (C-171): The composition-171 was prepared by combining *Brassica nigra* 90% aqueous ethanol extract (B.N-2) and *Tamarindus indica* 90% aqueous ethanol extract (T.I-2) in the ratio of 3:1.

Composition-172 (C-172): The composition-172 was prepared by combining *Brassica nigra* 90% aqueous ethanol extract (B.N-2) and *Tamarindus indica* 90% aqueous ethanol extract (T.I-2) in the ratio of 2:1.

Composition-173 (C-173): The composition-173 was prepared by combining *Brassica nigra* 90% aqueous ethanol extract (B.N-2) and *Tamarindus indica* 90% aqueous ethanol extract (T.I-2) in the ratio of 1:1.

Composition-174 (C-174): The composition-174 was prepared by combining *Brassica nigra* 90% aqueous ethanol extract (B.N-2) and *Tamarindus indica* 90% aqueous ethanol extract (T.I-2) in the ratio of 1:2.

Composition-175 (C-175): The composition-175 was prepared by combining *Brassica nigra* 90% aqueous ethanol extract (B.N-2) and *Tamarindus indica* 90% aqueous ethanol extract (T.I-2) in the ratio of 1:3.

Composition-176 (C-176): The composition-176 was prepared by combining *Brassica nigra* 90% aqueous ethanol extract (B.N-2) and *Cinnamomum tamala* 90% aqueous ethanol extract (C.T-1) in the ratio of 3:1.

Composition-177 (C-177): The composition-177 was prepared by combining *Brassica nigra* 90% aqueous ethanol extract (B.N-2) and *Cinnamomum tamala* 90% aqueous ethanol extract (C.T-1) in the ratio of 2:1.

Composition-178 (C-178): The composition-178 was prepared by combining *Brassica nigra* 90% aqueous ethanol extract (B.N-2) and *Cinnamomum tamala* 90% aqueous ethanol extract (C.T-1) in the ratio of 1:1.

Composition-179 (C-179): The composition-179 was prepared by combining *Brassica nigra* 90% aqueous ethanol extract (B.N-2) and *Cinnamomum tamala* 90% aqueous ethanol extract (C.T-1) in the ratio of 1:2.

Composition-180 (C-180): The composition-180 was prepared by combining *Brassica nigra* 90% aqueous ethanol extract (B.N-2) and *Cinnamomum tamala* 90% aqueous ethanol extract (C.T-1) in the ratio of 1:3.

Example 20: Preparation of the Compositions Containing Extracts of *Mangifera indica* in Combination with *Allium cepa, Tamarindus indica* and *Cinnamomum tamala*

Composition-181 (C-181): The composition-181 was prepared by combining *Mangifera indica* 50% aqueous ethanol extract (M.I-1) and *Allium cepa* water extract (A.C-1) in the ratio of 3:1.

Composition-182 (C-182): The composition-182 was prepared by combining *Mangifera indica* 50% aqueous ethanol extract (M.I-1) and *Allium cepa* water extract (A.C-1) in the ratio of 2:1.

Composition-183 (C-183): The composition-183 was prepared by combining *Mangifera indica* 50% aqueous ethanol extract (M.I-1) and *Allium cepa* water extract (A.C-1) in the ratio of 1:1.

Composition-184 (C-184): The composition-184 was prepared by combining *Mangifera indica* 50% aqueous ethanol extract (M.I-1) and *Allium cepa* water extract (A.C-1) in the ratio of 1:2.

Composition-185 (C-185): The composition-185 was prepared by combining *Mangifera indica* 50% aqueous ethanol extract (M.I-1) and *Allium cepa* water extract (A.C-1) in the ratio of 1:3.

Composition-186 (C-186): The composition-186 was prepared by combining *Mangifera indica* 50% aqueous ethanol extract (M.I-1) and *Tamarindus indica* 90% aqueous ethanol extract (T.I-2) in the ratio of 3:1.

Composition-187 (C-187): The composition-187 was prepared by combining *Mangifera indica* 50% aqueous ethanol extract (M.I-1) and *Tamarindus indica* 90% aqueous ethanol extract (T.I-2) in the ratio of 2:1.

Composition-188 (C-188): The composition-188 was prepared by combining *Mangifera indica* 50% aqueous ethanol extract (M.I-1) and *Tamarindus indica* 90% aqueous ethanol extract (T.I-2) in the ratio of 1:1.

Composition-189 (C-189): The composition-189 was prepared by combining *Mangifera indica* 50% aqueous ethanol extract (M.I-1) and *Tamarindus indica* 90% aqueous ethanol extract (T.I-2) in the ratio of 1:2.

Composition-190 (C-190): The composition-190 was prepared by combining *Mangifera indica* 50% aqueous ethanol extract (M.I-1) and *Tamarindus indica* 90% aqueous ethanol extract (T.I-2) in the ratio of 1:3.

Composition-191 (C-191): The composition-191 was prepared by combining *Mangifera indica* 50% aqueous ethanol extract (M.I-1) and *Cinnamomum tamala* 90% aqueous ethanol extract (C.T-1) in the ratio of 3:1.

Composition-192 (C-192): The composition-192 was prepared by combining *Mangifera indica* 50% aqueous ethanol extract (M.I-1) and *Cinnamomum tamala* 90% aqueous ethanol extract (C.T-1) in the ratio of 2:1.

Composition-193 (C-193): The composition-193 was prepared by combining *Mangifera indica* 50% aqueous ethanol extract (M.I-1) and *Cinnamomum tamala* 90% aqueous ethanol extract (C.T-1) in the ratio of 1:1.

Composition-194 (C-194): The composition-194 was prepared by combining *Mangifera indica* 50% aqueous ethanol extract (M.I-1) and *Cinnamomum tamala* 90% aqueous ethanol extract (C.T-1) in the ratio of 1:2.

Composition-195 (C-195): The composition-195 was prepared by combining *Mangifera indica* 50% aqueous ethanol extract (M.I-1) and *Cinnamomum tamala* 90% aqueous ethanol extract (C.T-1) in the ratio of 1:3.

Example 21: Preparation of the Compositions Containing Extracts of *Punica Granatum* in Combination with *Brassica nigra, Cinnamomum Zeylanicum, Nigella Sativa* and *Cinnamomum tamala* Along with Excipients Composition 196 (C-196): The composition-196 was prepared by combining 60 g of 70% aqueous ethanol extract of *Punica granatum*(P.G-4), 20 g of 90% aqueous ethanol extract of *Brassica nigra* (B.N-2), 13 g of maltodextrin, 3 g of carboxymethyl cellulose sodium (NaC M C), 2 g of magnesium hydroxide and 2 g of Syloid.

Composition 197 (C-197): The composition-197 was prepared by combining 60 g of 70% aqueous ethanol extract of *Punica granatum*(P.G-4), 20 g of 90% aqueous ethanol extract of *Cinnamomum zeylanicum* (C.Z-2), 13 g of maltodextrin, 3 g of carboxymethylcellulose sodium (NaC M C), 2 g of magnesium hydroxide and 2 K g of Syloid.

Composition 198 (C-198): The composition-198 was prepared by combining 60 g of 70% aqueous ethanol extract of *Punica granatum* (P.G-4), 20 g of water extract of *Nigella sativa* (N.S-1), 13 g of maltodextrin, 3 g of carboxymethylcellulose sodium (NaC MC), 2 g of magnesium hydroxide and 2 g of Syloid.

Composition 199 (C-199): The composition-199 was prepared by combining 60 g of 70% aqueous ethanol extract of *Punica granatum*(P.G-4), 20 g of 90% aqueous ethanol extract of *Cinnamomum tamala* (C.T-1), 13 g of maltodextrin, 3 g of carboxymethyl cellulose sodium (NaC M C), 2 g of magnesium hydroxide and 2 g of Syloid.

Example 22: General Procedure for Testosterone Assay

The herbs extracts and their compositions were evaluated for their ability to induce testosterone production in MA-10 mouse leydig cell line (ATCC, Manassas, Va., USA). The cells were cultured in 0.1% gelatin coated flasks in presence of DMEM: F12 medium (ATCC, Manassas, Va., USA) supplemented with 15% horse serum and 20 mM HEPES at 37° C. in a $CO_2$ incubator. Equal number of cells was plated in each well of a gelatin coated 96-well cell culture plate and allowed to attach overnight. The washed cells were supplemented with serum free-DMEM: F12 medium and treated with different concentrations of the test samples and incubated further for 48 h. Culture wells receiving 0.2% DMSO was considered as vehicle control and luteinizing hormone was used as positive control. The culture supernatants were collected, clarified at 10000 g for 5 min at 4° C., and used for Testosterone estimation using a specific commercially available ELISA kit. ELISA was performed using Testosterone EIA kit (Cayman chemicals, Ann Arbor, Mich., USA) according to the manufacturers protocol. This assay is based on competition between testosterone and a testosterone-Acetylcholinesterase (AchE) conjugate (Testosterone tracer) for a limited amount of testosterone anti body. Ellman˘ s reagent containing the substrate of AchE is used to detect the enzyme activity. The product of the enzyme reaction is yellow in color and absorbs strongly at 412 nm. The intensity of the color is proportional to the amount of the Testosterone tracer bound to the well and inversely proportional to the testosterone available in the test samples. Fifty microliters samples of cell free culture supernatants were used to estimate the Testosterone content. A standard curve was plotted with a set of known concentrations of testosterone standards as per protocol. The reported sensitivity of the assay kit was 6 pg/ml. The results are summarized in Table 2-13.

TABLE 2

Testosterone activity of the compositions containing *Punica granatum* and *Cinnamomum zeylanicum*.

| Comp # | | % increase | | % increase | Ratio | Comp Dose | g/mL | % increase of testosterone over control | |
|---|---|---|---|---|---|---|---|---|---|
| | | | | | | | | Additive (Calculated) | Observed |
| | P.G-1 | | C.Z-1 | | | | | | |
| C-1 | 1.25 | 4.05 | 3.75 | 6.82 | 1:3 | 5 | | 10.87 | 20.54 |
| C-2 | 1.66 | 5.37 | 3.34 | 6.07 | 1:2 | 5 | | 11.44 | 22.46 |
| C-3 | 2.5 | 8.1 | 2.5 | 4.55 | 1:1 | 5 | | 12.65 | 22.58 |
| C-4 | 3.34 | 10.82 | 1.66 | 3.02 | 2:1 | 5 | | 13.84 | 25.12 |
| C-5 | 3.75 | 12.15 | 1.25 | 2.27 | 3:1 | 5 | | 14.42 | 24.92 |
| | P.G-4 | | C.Z-2 | | | | | | |
| C-6 | 0.75 | 6.03 | 0.25 | 3.12 | 3:1 | 1 | | 9.15 | 19.26 |
| C-7 | 0.67 | 5.42 | 0.33 | 3.99 | 2:1 | 1 | | 9.41 | 15.72 |
| C-8 | 0.5 | 4.04 | 0.5 | 6.05 | 1:1 | 1 | | 10.09 | 21.68 |
| C-9 | 0.33 | 2.67 | 0.67 | 8.11 | 1:2 | 1 | | 10.78 | 23.30 |
| | P.G-6 | | C.Z-4 | | | | | | |
| C-17 | 0.67 | 7.40 | 0.33 | 10.91 | 2:1 | 1 | | 18.31 | 24.48 |
| C-19 | 0.07 | 1.06 | 0.13 | 17.99 | 1:2 | 0.2 | | 19.05 | 30.09 |

TABLE 3

Testosterone activity of the compositions of *Punica granatum* and *Nigella sativa*.

| Comp # | | % increase | | % increase | Ratio | Comp Dose | g/mL | % increase of testosterone over control | |
|---|---|---|---|---|---|---|---|---|---|
| | | | | | | | | Additive (Calculated) | Observed |
| | P.G-1 | | N.S-1 | | | | | | |
| C-22 | 1.66 | 5.37 | 3.34 | 8.87 | 1:2 | 5 | | 14.24 | 17.33 |
| C-23 | 2.5 | 8.1 | 2.5 | 6.64 | 1:1 | 5 | | 14.74 | 25.37 |
| C-24 | 3.34 | 10.82 | 1.66 | 4.41 | 2:1 | 5 | | 15.23 | 25.58 |
| C-25 | 3.75 | 12.15 | 1.25 | 3.32 | 3:1 | 5 | | 15.47 | 26.54 |
| | P.G-4 | | N.S-1 | | | | | | |
| C-26 | 3.75 | 12.84 | 1.25 | 5.02 | 3:1 | 5 | | 17.86 | 27.38 |
| C-27 | 0.13 | 7.47 | 0.07 | 8.89 | 2:1 | 0.2 | | 16.36 | 25.32 |
| C-28 | 2.5 | 8.56 | 2.5 | 10.05 | 1:1 | 5 | | 18.61 | 33.59 |
| C-29 | 0.33 | 2.64 | 0.67 | 10.30 | 1:2 | 1 | | 12.94 | 20.62 |
| C-30 | 0.05 | 2.87 | 0.15 | 19.05 | 1:3 | 0.2 | | 21.92 | 27.79 |

TABLE 3-continued

Testosterone activity of the compositions of *Punica granatum* and *Nigella sativa*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|---|---|
| | P.G-6 | | | N.S-1 | | | | | | | |
| C-32 | | 0.67 | 7.40 | | 0.33 | 3.64 | 2:1 | | 1 | 11.04 | 31.85 |
| C-33 | | 0.5 | 5.52 | | 0.5 | 5.52 | 1:1 | | 1 | 11.04 | 25.62 |
| C-34 | | 0.33 | 3.64 | | 0.67 | 7.40 | 1:2 | | 1 | 11.04 | 22.19 |
| | P.G-4 | | | N.S-2 | | | | | | | |
| C-35A | | 0.67 | 2.86 | | 0.33 | 4.09 | 2:1 | | 1 | 6.95 | 15.85 |
| C-35B | | 0.5 | 2.13 | | 0.5 | 6.22 | 1:1 | | 1 | 8.35 | 19.45 |
| C-35C | | 0.33 | 1.40 | | 0.67 | 8.33 | 1:2 | | 1 | 9.73 | 18.06 |

TABLE 4

Testosterone activity of the compositions of *Punica granatum* and *Brassica nigra*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|---|---|
| | P.G-1 | | | B.N-1 | | | | | | | |
| C-40 | | 3.75 | 12.15 | | 1.25 | 4.15 | 3:1 | | 5 | 16.3 | 23.27 |
| | P.G-4 | | | B.N-2 | | | | | | | |
| C-41 | | 0.75 | 5.99 | | 0.25 | 2.16 | 3:1 | | 1 | 8.15 | 23.01 |
| C-42 | | 0.67 | 5.35 | | 0.33 | 2.85 | 2:1 | | 1 | 8.2 | 15.75 |
| C-43 | | 0.5 | 3.99 | | 0.5 | 4.32 | 1:1 | | 1 | 8.31 | 14.99 |
| C-44 | | 0.33 | 2.64 | | 0.67 | 5.79 | 1:2 | | 1 | 8.43 | 17.74 |
| | P.G-6 | | | B.N-4 | | | | | | | |
| C-47 | | 0.67 | 9.04 | | 0.33 | 1.40 | 2:1 | | 1 | 10.44 | 21.12 |
| C-48 | | 0.5 | 6.74 | | 0.5 | 2.13 | 1:1 | | 1 | 8.87 | 19.7 |
| C-49 | | 0.33 | 4.45 | | 0.67 | 2.85 | 1:2 | | 1 | 7.30 | 17.54 |
| | P.G-7 | | | B.N-4 | | | | | | | |
| C-52 | | 0.67 | 5.84 | | 0.33 | 1.40 | 2:1 | | 1 | 7.24 | 14.88 |
| C-53 | | 0.5 | 4.36 | | 0.5 | 2.13 | 1:1 | | 1 | 6.49 | 19.44 |
| C-54 | | 0.33 | 2.88 | | 0.67 | 2.85 | 1:2 | | 1 | 5.73 | 17.14 |
| | P.G-4 | | | B.N-5 | | | | | | | |
| C-57 | | 0.13 | 12.36 | | 0.07 | 3.23 | 2:1 | | 0.2 | 15.59 | 21.30 |
| C-58 | | 0.1 | 9.51 | | 0.1 | 4.61 | 1:1 | | 0.2 | 14.12 | 24.29 |
| C-59 | | 0.07 | 6.66 | | 0.13 | 5.99 | 1:2 | | 0.2 | 12.65 | 26.52 |

TABLE 5

Testosterone activity of the compositions of *Punica granatum* and *Mangifera indica*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|---|---|
| | P.G-4 | | | M.I-1 | | | | | | | |
| C-62 | | 0.67 | 2.86 | | 0.33 | 4.26 | 2:1 | | 1 | 7.12 | 15.71 |
| C-63 | | 0.5 | 2.13 | | 0.5 | 6.45 | 1:1 | | 1 | 8.58 | 18.31 |
| C-64 | | 0.33 | 1.40 | | 0.67 | 8.65 | 1:2 | | 1 | 10.05 | 20.45 |

TABLE 5-continued

Testosterone activity of the compositions of *Punica granatum* and *Mangifera indica*.

| Comp # | % | | % | | Comp Ratio | Dose | % increase of testosterone over control | |
|---|---|---|---|---|---|---|---|---|
| | | | | | | | Additive | |
| | | g/mL | increase | | g/mL | increase | | g/mL | (Calculated) | Observed |
| | P.G-6 | | M.I-3 | | | | | |
| C-67 | 3.33 | 5.29 | 1.67 | 5.05 | 2:1 | 5 | 10.34 | 28.37 |
| C-68 | 0.1 | 7.85 | 0.1 | 5.12 | 1:1 | 0.2 | 12.97 | 20.41 |
| C-69 | 0.07 | 5.50 | 0.13 | 6.66 | 1:2 | 0.2 | 12.16 | 23.25 |
| | P.G-4 | | M.I-4 | | | | | |
| C-70A | 0.67 | 2.86 | 0.33 | 3.29 | 2:1 | 1 | 6.15 | 14.65 |
| C-70B | 0.33 | 1.40 | 0.67 | 7.45 | 1:2 | 1 | 8.85 | 17.54 |

TABLE 6

Testosterone activity of the compositions containing *Cinnamomum zeylanicum* in combination with *Brassica nigra*, *Nigella sativa* and *Mangifera indica*.

| Comp # | % | | % | | Comp Ratio | Dose | % increase of testosterone over control | |
|---|---|---|---|---|---|---|---|---|
| | | g/mL | increase | | g/mL | increase | | g/mL | Additive (Calculated) | Observed |
| | C.Z-1 | | B.N-1 | | | | | |
| C-74 | 0.13 | 3.00 | 0.07 | 3.90 | 2:1 | 0.2 | 6.90 | 14.5 |
| C-75 | 0.15 | 3.47 | 0.05 | 2.79 | 3:1 | 0.2 | 6.26 | 18.5 |
| | C.Z-2 | | B.N-2 | | | | | |
| C-77 | 0.13 | 3.58 | 0.07 | 2.31 | 2:1 | 0.2 | 5.89 | 13.81 |
| C-79 | 0.33 | 1.32 | 0.67 | 7.68 | 1:2 | 1 | 9.00 | 15.38 |
| | C.Z-2 | | N.S-1 | | | | | |
| C-81 | 0.75 | 5.86 | 0.25 | 5.88 | 3:1 | 1 | 11.74 | 20.41 |
| C-82 | 0.67 | 5.23 | 0.33 | 7.76 | 2:1 | 1 | 12.99 | 23.8 |
| C-83 | 0.1 | 5.86 | 0.1 | 11.02 | 1:1 | 0.2 | 16.88 | 24.44 |
| C-84 | 0.07 | 4.10 | 0.13 | 14.32 | 1:2 | 0.2 | 18.42 | 31.74 |
| C-85 | 0.05 | 2.93 | 0.15 | 16.53 | 1:3 | 0.2 | 19.46 | 40.33 |
| | C.Z-2 | | M.I-1 | | | | | |
| C-87 | 0.67 | 2.69 | 0.33 | 4.26 | 2:1 | 1 | 6.95 | 16.33 |
| C-88 | 0.1 | 2.75 | 0.1 | 3.95 | 1:1 | 0.2 | 6.7 | 17.56 |
| C-89 | 0.07 | 2.77 | 0.13 | 5.14 | 1:2 | 0.2 | 7.91 | 12.17 |

TABLE 7

Testosterone activity of the compositions containing *Nigella sativa* in combination with *Brassica nigra*, and *Mangifera indica*.

| Comp # | % | | % | | Comp Ratio | Dose | % increase of testosterone over control | |
|---|---|---|---|---|---|---|---|---|
| | | g/mL | increase | | g/mL | increase | | g/mL | Additive (Calculated) | Observed |
| | N.S-1 | | B.N-1 | | | | | |
| C-91 | 0.05 | 5.26 | 0.15 | 2.79 | 3:1 | 0.2 | 8.05 | 13.8 |
| C-93 | 2.5 | 6.64 | 2.5 | 8.31 | 1:1 | 5 | 14.95 | 23.93 |
| C-94 | 0.12 | 2.45 | 0.06 | 7.26 | 1:2 | 0.2 | 9.71 | 14.46 |
| C-95 | 0.15 | 1.75 | 0.05 | 8.37 | 1:3 | 0.2 | 10.12 | 10.67 |

TABLE 7-continued

Testosterone activity of the compositions containing *Nigella sativa* in combination with *Brassica nigra*, and *Mangifera indica*.

| Comp # | N.S-1 g/mL | % increase | B.N-2 g/mL | % increase | Ratio | Comp Dose g/mL | % increase of testosterone over control Additive (Calculated) | Observed |
|---|---|---|---|---|---|---|---|---|
| C-97 | 0.67 | 11.76 | 0.33 | 11.19 | 2:1 | 1 | 22.95 | 33.33 |
| C-98 | 0.5 | 8.77 | 0.5 | 16.95 | 1:1 | 1 | 25.72 | 34.48 |
| C-99 | 0.33 | 5.79 | 0.67 | 22.72 | 1:2 | 1 | 28.51 | 35.46 |
|  | N.S-1 |  | M.I-1 |  |  |  |  |  |
| C-102 | 0.13 | 16.57 | 0.07 | 1.85 | 2:1 | 0.2 | 18.42 | 39.66 |
| C-103 | 0.1 | 12.75 | 0.1 | 2.65 | 1:1 | 0.2 | 15.4 | 29.02 |
| C-104 | 0.07 | 8.92 | 0.13 | 3.44 | 1:2 | 0.2 | 12.36 | 23.43 |

TABLE 8

Testosterone activity of the compositions containing *Brassica nigra* and *Mangifera indica*.

| Comp # | B.N-1 g/mL | % increase | M.I-1 g/mL | % increase | Ratio | Comp Dose g/mL | % increase of testosterone over control Additive (Calculated) | Observed |
|---|---|---|---|---|---|---|---|---|
| C-107 | 0.67 | 22.72 | 0.33 | 13.52 | 2:1 | 1 | 36.24 | 41.66 |
| C-108 | 0.5 | 16.95 | 0.5 | 20.48 | 1:1 | 1 | 37.43 | 49.50 |
| C-109 | 0.33 | 11.19 | 0.67 | 27.45 | 1:2 | 1 | 38.64 | 47.86 |

TABLE 9

Testosterone activity of the compositions containing *Punica granatum* in combination with *Allium cepa*, *Tamarindus indica* and *Cinnamomum tamala*.

| Comp # | P.G-4 g/mL | % increase | A.C-1 g/mL | % increase | Ratio | Comp Dose g/mL | % increase of testosterone over control Additive (Calculated) | Observed |
|---|---|---|---|---|---|---|---|---|
| C-112 | 0.67 | 5.42 | 0.33 | 5.78 | 2:1 | 1 | 11.2 | 16.64 |
| C-113 | 0.5 | 4.04 | 0.5 | 8.76 | 1:1 | 1 | 12.8 | 26.63 |
| C-114 | 0.33 | 2.67 | 0.67 | 11.74 | 1:2 | 1 | 14.41 | 20.32 |
|  | P.G-4 |  | T.I-2 |  |  |  |  |  |
| C-117 | 0.67 | 5.42 | 0.33 | 3.48 | 2:1 | 1 | 8.9 | 12.15 |
| C-118 | 0.5 | 4.04 | 0.5 | 5.27 | 1:1 | 1 | 9.31 | 20.84 |
| C-119 | 0.33 | 2.67 | 0.67 | 7.07 | 1:2 | 1 | 9.74 | 21.47 |
|  | P.G-4 |  | C.T-1 |  |  |  |  |  |
| C-121 | 3.75 | 5.03 | 1.25 | 1.99 | 3:1 | 5 | 7.02 | 24.05 |
| C-122 | 3.33 | 4.46 | 1.67 | 2.66 | 2:1 | 5 | 7.12 | 19.23 |
| C-123 | 0.1 | 5.31 | 0.1 | 3.66 | 1:1 | 0.2 | 8.97 | 19.73 |
| C-124 | 1.67 | 2.24 | 3.33 | 5.32 | 1:2 | 5 | 7.56 | 17.48 |
| C-125 | 0.25 | 3.80 | 0.75 | 9.44 | 1:3 | 1 | 13.24 | 20.68 |
|  | P.G-6 |  | C.T-4 |  |  |  |  |  |
| C-127 | 0.67 | 7.40 | 0.33 | 6.30 | 2:1 | 1 | 13.7 | 30.84 |
| C-128 | 2.5 | 10.77 | 2.5 | 9.14 | 1:1 | 5 | 19.91 | 33.18 |
| C-129 | 0.33 | 3.64 | 0.67 | 12.78 | 1:2 | 1 | 16.42 | 32.1 |

TABLE 10

Testosterone activity at the compositions containing *Cinnamomum zeylanicum* in combination with *Allium cepa*, *Tamarindus indica* and *Cinnamomum tamala*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|
| | C.Z -2 | | A.C-1 | | | | |
| C-136 | 0.75 | 5.86 | 0.25 | 5.17 | 3:1 | 1 | 11.03 | 29.65 |
| C-137 | 0.13 | 7.62 | 0.07 | 7.53 | 2:1 | 0.2 | 15.15 | 27.05 |
| C-138 | 0.5 | 3.91 | 0.5 | 10.33 | 1:1 | 1 | 14.24 | 28.37 |
| C-139 | 1.67 | 5.17 | 3.33 | 11.33 | 1:2 | 5 | 16.5 | 27.38 |
| C-140 | 0.05 | 2.93 | 0.15 | 16.13 | 1:3 | 0.2 | 19.06 | 32.02 |
| | C.Z-2 | | T.I-2 | | | | |
| C-141 | 0.15 | 10.98 | 0.05 | 4.51 | 3:1 | 0.2 | 15.49 | 21.7 |
| C-142 | 0.13 | 9.52 | 0.07 | 6.31 | 2:1 | 0.2 | 15.83 | 27.29 |
| C-143 | 0.1 | 7.32 | 0.1 | 9.02 | 1:1 | 0.2 | 16.34 | 41.55 |
| C-144 | 0.07 | 5.13 | 0.13 | 11.73 | 1:2 | 0.2 | 16.86 | 38.57 |
| | C.Z-2 | | C.T-1 | | | | |
| C-146 | 0.75 | 14.58 | 0.25 | 4.01 | 3:1 | 1 | 18.59 | 25.96 |
| C-147 | 3.33 | 11.62 | 1.67 | 7.50 | 2:1 | 5 | 19.12 | 32.83 |
| C-148 | 0.5 | 9.72 | 0.5 | 8.02 | 1:1 | 1 | 17.74 | 29.95 |
| C-149 | 0.33 | 6.41 | 0.67 | 10.74 | 1:2 | 1 | 17.15 | 37.58 |
| C-150 | 0.25 | 4.86 | 0.75 | 12.03 | 1:3 | 1 | 16.89 | 50.85 |

TABLE 11

Testosterone activity of the compositions containing *Nigella sativa* in combination with *Allium cepa*, *Tamarindus indica* and *Cinnamomum tamala*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|
| | N.S-1 | | A.C-1 | | | | |
| C-151 | 3.75 | 17.54 | 1.25 | 8.20 | 3:1 | 5 | 25.74 | 39.16 |
| C-152 | 3.33 | 14.55 | 1.67 | 10.29 | 2:1 | 5 | 24.84 | 29.16 |
| | N.S-1 | | T.I-2 | | | | |
| C-157 | 3.33 | 10.59 | 1.67 | 7.43 | 2:1 | 5 | 18.02 | 21.66 |
| C-158 | 2.5 | 7.95 | 2.5 | 11.13 | 1:1 | 5 | 19.08 | 29.19 |
| C-159 | 1.67 | 5.31 | 3.33 | 14.83 | 1:2 | 5 | 20.14 | 25.35 |
| C-160 | 0.25 | 5.7 | 0.75 | 9.49 | 1:3 | 1 | 15.19 | 22.39 |
| | N.S-1 | | C.T-1 | | | | |
| C-162 | 0.67 | 15.27 | 0.33 | 4.34 | 2:1 | 1 | 19.61 | 28.04 |
| C-163 | 2.5 | 7.95 | 2.5 | 6.65 | 1:1 | 5 | 14.6 | 27.53 |
| C-164 | 0.07 | 5.48 | 0.13 | 11.46 | 1:2 | 0.2 | 16.94 | 33.04 |
| C-165 | 0.05 | 3.92 | 0.15 | 13.22 | 1:3 | 0.2 | 17.14 | 33.75 |
| | N.S-2 | | AC-3 | | | | |
| C-155A | 3.33 | 6.60 | 1.67 | 0.35 | 2:1 | 5 | 6.95 | 16.85 |
| C-155B | 2.5 | 4.95 | 2.5 | 0.52 | 1:1 | 5 | 5.47 | 14.75 |
| C-155C | 1.67 | 3.31 | 3.33 | 0.69 | 1:2 | 5 | 4.00 | 15.05 |

TABLE 12

Testosterone activity of the compositions containing *Brassica nigra* in combination with *Allium cepa*, *Tamarindus indica* and *Cinnamomum tamala*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|---|---|
| | B.N-2 | | | A.C-1 | | | | | | | |
| C-166 | | 0.75 | 12.53 | | 0.25 | 3.78 | 3:1 | | 1 | 16.31 | 35.68 |
| C-167 | | 0.67 | 11.19 | | 0.33 | 4.99 | 2:1 | | 1 | 16.18 | 36.31 |
| C-168 | | 0.5 | 8.35 | | 0.5 | 7.57 | 1:1 | | 1 | 15.92 | 32.97 |
| C-169 | | 0.33 | 5.51 | | 0.67 | 10.14 | 1:2 | | 1 | 15.65 | 25.23 |
| | B.N-2 | | | T.I-2 | | | | | | | |
| C-171 | | 3.75 | 8.04 | | 1.25 | 5.28 | 3:1 | | 5 | 13.32 | 16.17 |
| C-172 | | 3.33 | 7.14 | | 1.67 | 7.05 | 2:1 | | 5 | 14.19 | 24.71 |
| C-173 | | 2.5 | 5.36 | | 2.5 | 10.56 | 1:1 | | 5 | 15.92 | 27.02 |
| C-174 | | 0.33 | 3.70 | | 0.67 | 7.24 | 1:2 | | 1 | 10.94 | 24.14 |
| C-175 | | 0.25 | 2.80 | | 0.75 | 8.11 | 1:3 | | 1 | 10.91 | 12.54 |
| | B.N-2 | | | C.T-1 | | | | | | | |
| C-176 | | 3.75 | 8.04 | | 1.25 | 2.58 | 3:1 | | 5 | 10.62 | 29.97 |
| C-177 | | 3.33 | 7.14 | | 1.67 | 3.44 | 2:1 | | 5 | 10.58 | 29.16 |
| C-178 | | 2.5 | 5.36 | | 2.5 | 5.15 | 1:1 | | 5 | 10.51 | 30.18 |
| C-179 | | 1.67 | 3.58 | | 3.33 | 6.87 | 1:2 | | 5 | 10.45 | 24.66 |

TABLE 13

Testosterone activity of the compositions containing *Mangifera indica* in combination with *Allium cepa*, *Tamarindus indica* and *Cinnamomum tamala*.

| Comp # | | g/mL | % increase | | g/mL | % increase | Ratio | Comp Dose | g/mL | % increase of testosterone over control Additive (Calculated) | Observed |
|---|---|---|---|---|---|---|---|---|---|---|---|
| | M.I-1 | | | A.C-1 | | | | | | | |
| C-182 | | 0.67 | 28.65 | | 0.33 | 10.35 | 2:1 | | 1 | 39.00 | 49.55 |
| C-183 | | 0.5 | 21.38 | | 0.5 | 15.68 | 1:1 | | 1 | 37.06 | 43.47 |
| C-184 | | 0.33 | 14.11 | | 0.67 | 21.02 | 1:2 | | 1 | 35.13 | 41.38 |
| | M.I-1 | | | T.I-2 | | | | | | | |
| C-187 | | 3.33 | 27.64 | | 1.67 | 20.16 | 2:1 | | 5 | 47.8 | 69.05 |
| C-188 | | 2.5 | 20.75 | | 2.5 | 30.17 | 1:1 | | 5 | 50.92 | 58.21 |
| C-189 | | 0.33 | 14.11 | | 0.67 | 32.22 | 1:2 | | 1 | 46.33 | 59.47 |
| | M.I-1 | | | C.T-1 | | | | | | | |
| C-192 | | 0.13 | 29.28 | | 0.07 | 15.05 | 2:1 | | 0.2 | 44.33 | 51.56 |
| C-193 | | 2.5 | 20.75 | | 2.5 | 30.17 | 1:1 | | 5 | 50.92 | 61.08 |
| C-194 | | 1.67 | 13.86 | | 3.33 | 40.19 | 1:2 | | 5 | 54.05 | 64.88 |

Example 23: General Procedure for Aromatase Inhibition Assay

Aromatase inhibition was determined using intact cells in culture as described by Samson et al., (Samson M. et al., J. Steroid Biochem Mol. Biol. 2009, 116, 154-159) with modifications. Briefly, placental choriocarcinoma (JEG-3) cells (ATCC; Cat #HTB-36) were harvested from the culture flasks and 40000 cells/well were seeded in a 96-well plate in 2001 L of EMEM (Hi-Media; Cat #AL047S)+5% Charcoal-stripped FBS (Thermo Fisher; Cat #12676011) medium and incubated for 48 hours in a $CO_2$ incubator. After the incubation, older medium was replenished with 1501 L of fresh EMEM+5% Charcoal-stripped F B S medium. Cells were treated with different concentrations of test samples and incubated for 1 hour in a $CO_2$ incubator (pre-treatment). Independently, cells were also treated with different concentrations of Letrozole (Sigma; Cat #L6545-10MG), an aromatase inhibitor. After the incubation, all the cells were treated with 50 nM 4-Androstene-3, 17-dione (Induction; Sigma Cat #46033-250MG), a substrate for aromatase except for vehicle control (Cells+0.2% DMSO) and incubated for 48 hours in a $CO_2$ incubator. After 48 hours, the culture plate was centrifuged at 270×g for 10 minutes and the cell-free supernatants were collected and stored at −80èC freezer until analysis. Enzyme immunoassay (EIA) was performed for Estrone using the EIA kit from Arbor assays (Cat #K 031-H5) according to the manufacturer˘ s protocol. Percent inhibition of aromatase was calculated by the following formula:

% Inhibition of Aromatase=[(Normalized Concn. of Estrone in Induction)−(Normalized Concn. of Estrone in Test samples)]/(Normalized Concn. of Estrone in Induction)× 100. The results are presented in tables 14-18.

TABLE 14

Aromatase inhibition activity of the of the compositions containing
Punica granatum in combination with Allium cepa, Tamarindus indica and
Cinnamomum tamala.

| Comp # | µg/mL | % increase | µg/mL | % increase | Ratio | Comp Dose µg/mL | % Aromatase inhibition Additive (Calculated) | Observed |
|---|---|---|---|---|---|---|---|---|
| | P.G-4 | | A.C-1 | | | | | |
| C-112 | 16.67 | 15.60 | 8.33 | 5.77 | 2:1 | 25 | 21.37 | 30.15 |
| C-113 | 12.5 | 11.7 | 12.5 | 8.66 | 1:1 | 25 | 20.36 | 30.06 |
| C-114 | 1.67 | 6.08 | 3.33 | 10.06 | 1:2 | 5 | 16.14 | 27.51 |
| | P.G-4 | | T.I-2 | | | | | |
| C-117 | 0.67 | 8.31 | 0.33 | 6.34 | 2:1 | 1 | 14.65 | 29.02 |
| C-118 | 0.5 | 6.2 | 0.5 | 9.6 | 1:1 | 1 | 15.8 | 21.6 |
| C-119 | 0.33 | 4.09 | 0.67 | 12.86 | 1:2 | 1 | 16.95 | 28.4 |
| | P.G-4 | | C.T-1 | | | | | |
| C-121 | 0.75 | 4.78 | 0.25 | 0.41 | 3:1 | 1 | 5.19 | 10.41 |
| C-122 | 3.33 | 4.01 | 1.67 | 2.16 | 2:1 | 5 | 6.17 | 18.93 |
| C-123 | 0.5 | 3.19 | 0.5 | 0.82 | 1:1 | 1 | 4.01 | 16.5 |
| C-124 | 1.67 | 1.2 | 3.33 | 4.30 | 1:2 | 5 | 5.32 | 22.71 |
| C-125 | 0.25 | 1.59 | 0.75 | 1.01 | 1:3 | 1 | 2.60 | 11.14 |
| | P.G-6 | | C.T-4 | | | | | |
| C-127 | 16.67 | 12.88 | 8.33 | 7.15 | 2:1 | 25 | 20.03 | 32.25 |
| C-128 | 12.5 | 9.66 | 12.5 | 10.73 | 1:1 | 25 | 20.39 | 28.46 |
| C-129 | 8.33 | 6.44 | 16.67 | 14.32 | 1:2 | 25 | 20.76 | 27.8 |
| | P.G-4 | | C.T-3 | | | | | |
| C-132 | 3.33 | 5.16 | 1.67 | 2.59 | 2:1 | 5 | 7.75 | 25.96 |
| C-133 | 12.5 | 15.06 | 12.5 | 4.62 | 1:1 | 25 | 19.68 | 29.67 |
| C-134 | 8.33 | 10.03 | 16.67 | 6.17 | 1:2 | 25 | 16.2 | 30.17 |

TABLE 15

Aromatase inhibition activity of the of the compositions containing
Cinnamomum zeylanicum in combination with Allium cepa, Tamarindus indica and
Cinnamomum tamala.

| Comp # | µg/mL | % increase | µg/mL | % increase | Ratio | Comp Dose µg/mL | % Aromatase inhibition Additive (Calculated) | Observed |
|---|---|---|---|---|---|---|---|---|
| | C.Z-2 | | A.C-1 | | | | | |
| C-136 | 3.75 | 20.85 | 1.25 | 0.16 | 3:1 | 5 | 21.01 | 26.58 |
| C-137 | 16.67 | 24.63 | 8.33 | 0.0 | 2:1 | 25 | 24.63 | 32.38 |
| C-138 | 2.5 | 13.9 | 2.5 | 0.32 | 1:1 | 5 | 14.22 | 35.68 |
| C-139 | 1.67 | 9.18 | 3.33 | 0.43 | 1:2 | 5 | 9.61 | 35.13 |
| C-140 | 1.25 | 6.95 | 3.75 | 0.49 | 1:3 | 5 | 7.44 | 36.74 |
| | C.Z-2 | | T.I-2 | | | | | |
| C-141 | 18.75 | 10.45 | 6.25 | 9.6 | 3:1 | 25 | 20.05 | 30.33 |
| C-142 | 16.67 | 9.29 | 8.33 | 12.79 | 2:1 | 25 | 22.08 | 35.43 |
| C-143 | 12.5 | 6.97 | 12.5 | 19.2 | 1:1 | 25 | 26.17 | 34.93 |
| | 0.33 | 3.38 | 0.67 | 7.89 | 1:2 | 1 | 11.27 | 33.96 |
| | 0.25 | 2.56 | 0.75 | 8.83 | 1:3 | 1 | 11.39 | 35.71 |
| | C.Z-2 | | C.T-1 | | | | | |
| C-146 | 18.75 | 10.45 | 6.25 | 3.66 | 3:1 | 25 | 14.11 | 36.43 |
| C-147 | 16.67 | 9.29 | 8.33 | 4.88 | 2:1 | 25 | 14.17 | 33.53 |
| C-148 | 0.5 | 5.12 | 0.5 | 5.32 | 1:1 | 1 | 10.44 | 31.66 |
| C-149 | 8.33 | 4.64 | 16.67 | 9.76 | 1:2 | 25 | 14.4 | 62.57 |
| C-150 | 0.25 | 2.56 | 0.75 | 7.98 | 1:3 | 1 | 10.54 | 56.47 |

TABLE 16

Aromatase inhibition activity of the of the compositions containing *Nigella sativa* in combination with *Allium cepa*, *Tamarindus indica* and *Cinnamomum tamala*.

| Comp # | | g/mL | % increase | | g/mL | % increase | Ratio | Comp Dose | g/mL | % Aromatase inhibition Additive (Calculated) | Observed |
|---|---|---|---|---|---|---|---|---|---|
| | N.S-1 | | A.C-1 | | | | | |
| C-151 | 3.75 | 11.66 | 1.25 | 3.13 | 3:1 | 5 | 14.79 | 25.93 |
| C-152 | 3.33 | 10.35 | 1.67 | 4.18 | 2:1 | 5 | 14.53 | 32.14 |
| C-153 | 2.5 | 7.77 | 2.5 | 6.26 | 1:1 | 5 | 14.03 | 45.78 |
| C-154 | 1.67 | 5.19 | 3.33 | 8.33 | 1:2 | 5 | 13.52 | 43.8 |
| C-155 | 1.25 | 3.88 | 3.75 | 9.39 | 1:3 | 5 | 13.27 | 30.48 |
| | N.S-1 | | T.I-2 | | | | | |
| C-156 | 3.75 | 5.91 | 1.25 | 4.25 | 3:1 | 5 | 10.16 | 32.21 |
| C-157 | 3.33 | 5.24 | 1.67 | 5.68 | 2:1 | 5 | 10.92 | 43.54 |
| C-158 | 0.5 | 8.03 | 0.5 | 7.31 | 1:1 | 1 | 15.34 | 49.85 |
| C-159 | 0.33 | 5.29 | 0.67 | 9.79 | 1:2 | 1 | 15.08 | 58.72 |
| C-160 | 0.25 | 4.01 | 0.75 | 10.96 | 1:3 | 1 | 14.97 | 39.64 |
| | N.S-1 | | C.T-1 | | | | | |
| C-161 | 18.75 | 2.46 | 6.25 | 0.82 | 3:1 | 25 | 3.28 | 32.69 |
| C-162 | 16.67 | 2.18 | 8.33 | 1.09 | 2:1 | 25 | 3.27 | 29.96 |
| C-163 | 12.5 | 1.64 | 12.5 | 1.64 | 1:1 | 25 | 3.28 | 31.35 |
| C-164 | 8.33 | 1.09 | 16.67 | 2.18 | 1:2 | 25 | 3.27 | 34.63 |
| C-165 | 6.25 | 0.82 | 18.75 | 2.46 | 1:3 | 25 | 3.28 | 23.93 |

TABLE 17

Aromatase inhibition activity of the of the compositions containing *Brassica nigra* in combination with *Allium cepa*, *Tamarindus indica* and *Cinnamomum tamala*.

| Comp # | | g/mL | % increase | | g/mL | % increase | Ratio | Comp Dose | g/mL | % Aromatase inhibition Additive (Calculated) | Observed |
|---|---|---|---|---|---|---|---|---|---|
| | B.N-2 | | A.C-1 | | | | | |
| C-166 | 18.75 | 0.96 | 6.25 | 4.69 | 3:1 | 25 | 5.65 | 32.46 |
| C-167 | 16.67 | 0.85 | 8.33 | 6.26 | 2:1 | 25 | 7.11 | 34.9 |
| C-168 | 12.5 | 0.64 | 12.5 | 9.39 | 1:1 | 25 | 10.03 | 42.38 |
| C-169 | 8.33 | 0.42 | 16.67 | 12.52 | 1:2 | 25 | 12.94 | 41.72 |
| C-170 | 6.25 | 0.32 | 18.75 | 14.09 | 1:3 | 25 | 14.41 | 31.58 |
| | B.N-2 | | T.I-2 | | | | | |
| C-171 | 3.75 | 5.08 | 1.25 | 2.16 | 3:1 | 5 | 7.24 | 27.13 |
| C-172 | 3.33 | 4.50 | 1.67 | 2.88 | 2:1 | 5 | 7.38 | 34.32 |
| C-173 | 2.5 | 3.38 | 2.5 | 4.32 | 1:1 | 5 | 7.7 | 35.19 |
| C-174 | 1.67 | 2.26 | 3.33 | 5.75 | 1:2 | 5 | 8.01 | 39.53 |
| C-175 | 1.25 | 1.69 | 3.75 | 6.48 | 1:3 | 5 | 8.17 | 27.85 |
| | B.N-2 | | C.T-1 | | | | | |
| C-176 | 3.75 | 5.08 | 1.25 | 1.97 | 3:1 | 5 | 7.05 | 39.38 |
| C-177 | 3.33 | 4.50 | 1.67 | 2.63 | 2:1 | 5 | 7.13 | 26.29 |
| C-178 | 2.5 | 3.38 | 2.5 | 3.94 | 1:1 | 5 | 7.32 | 32.03 |
| C-179 | 1.67 | 2.26 | 3.33 | 5.24 | 1:2 | 5 | 7.50 | 23.93 |
| C-180 | 1.25 | 1.69 | 3.75 | 5.91 | 1:3 | 5 | 7.60 | 24.73 |

TABLE 18

Aromatase inhibition activity of the of the compositions containing
*Mangifera indica* in combination with *Allium cepa*, *Tamarindus indica* and
*Cinnamomum tamala*.

| Comp # | µg/mL | % increase | µg/mL | % increase | Ratio | Comp Dose µg/mL | % Aromatase inhibition Additive (Calculated) | Observed |
|---|---|---|---|---|---|---|---|---|
| | MI-1 | | A.C-1 | | | | | |
| C-182 | 16.67 | 10.63 | 8.33 | 5.77 | 2:1 | 25 | 16.4 | 27.05 |
| C-183 | 12.5 | 7.97 | 12.5 | 8.66 | 1:1 | 25 | 16.63 | 25.48 |
| C-184 | 8.33 | 5.31 | 16.67 | 11.55 | 1:2 | 25 | 16.86 | 30.26 |
| | MI-1 | | T.I-2 | | | | | |
| C-187 | 0.67 | 13.48 | 0.33 | 7.85 | 2:1 | 1 | 21.33 | 28.67 |
| C-188 | 2.5 | 10.02 | 2.5 | 13.42 | 1:1 | 5 | 23.44 | 36.11 |
| C-189 | 1.67 | 6.69 | 3.33 | 17.87 | 1:2 | 5 | 24.56 | 37.94 |
| | MI-1 | | C.T-1 | | | | | |
| C-192 | 3.33 | 13.35 | 1.67 | 8.76 | 2:1 | 5 | 22.11 | 31.17 |
| C-193 | 2.5 | 10.02 | 2.5 | 13.12 | 1:1 | 5 | 23.14 | 28.45 |
| C-194 | 1.67 | 6.69 | 3.33 | 17.47 | 1:2 | 5 | 24.16 | 32.84 |

Example-24: In Vivo Evaluation of Compositions-196 (C-196), Composition-197 (C-197), Composition-198 (C-198) and Composition-199 (C-199) for Testosterone Boosting in Sprague Dawley Rats Methods: Male Sprague Dawley rats were acclimatized and 56 animals were randomized into eight groups (G1 to G8). The treatment group animals were supplemented with C-196 (G2; 100 mg/kg), C-196 (G3; 200 mg/kg; p.o.), C-197 (G4; 100 mg/kg), C197 (C5; 200 mg/kg; p.o.), C-198 (G6; 100 mg/kg), C-198 (G7; 200 mg/kg; p.o.) or C-199 (G8; 200 mg/kg; p.o.) once daily for a 6 weeks all in 10 mL of vehicle (0.5% CMC sodium in water). The control group (G1) animals were supplemented with 10 mL of vehicle only. Blood samples were collected from all the animals; Serum separated and analyzed for testosterone levels by ELISA on day 43.

On the day of sacrifice, i.e., on day 43, animals were euthanized and caudal epididymides along with vas deferens (both side) were dissected out and semen squeezed out into Dulbecco's Phosphate Buffered Saline for analysis of sperm count.

Results: The results expressed as mean ± S.E.M. Data was subjected to statistical analysis using one way ANOVA followed by Dunnett's post-hoc test to draw a comparison of all the groups with Normal control (G1) using GraphPad Prism v 5.01 (GraphPad Software, Inc., CA, USA). $P<0.05$ was considered statistically significant. No abnormal clinical signs and weight difference were observed among all the groups throughout the treatment duration, indicating the safety of the test items, C-196, C-197, C-198 and C-199. All the treatment groups displayed increased testosterone levels in serum samples of day 43 [G2 (17.38%), G3 (33.79%), G4 (8.11%), G5 (77.38%), G6 (36.41%), G7 (5.83%) and G8 (41.70%)] over the control group. The testosterone levels exhibited by different treatment group are summarized in Table 19 and depicted in FIG. 1. Similarly, all the treatment groups showed improved sperm count when compared to the control group. However, the animals of groups, G3, G6, G7 and G8 treated with C-196 [200 mg/kg), C-198 (100 mg/kg), C198 (200 mg/kg) and C-199 (200 mg/kg) respectively displayed statistically significantly increases sperm count as summarized in Table 20 and depicted in FIG. 2.

TABLE 19

| Serum testosterone levels (ng/mL) | | |
|---|---|---|
| Group | Dose (mg/kg, p.o.) | Testosterone (ng/mL) |
| G1-Normal Control | — | 2.06 ± 0.48 |
| G2-C-196 | 100 | 2.42 ± 0.51 |
| G3-C-196 | 200 | 2.76 ± 0.82 |
| G4-C-197 | 100 | 2.23 ± 0.85 |
| G5-C-197 | 200 | 3.65 ± 1.72 |
| G6-C-198 | 100 | 2.81 ± 0.46 |
| G7-C-198 | 200 | 2.18 ± 0.22 |
| G8-C-199 | 200 | 2.92 ± 0.79 |

Data are expressed as mean ± S.E.M of seven rats per group.

TABLE 20

| Sperm Count | |
|---|---|
| Group | Count (millions/mL) |
| G1/Vehicle Control | 39.79 ± 2.73 |
| G2/C-196 (100 mg/kg) | 46.64 ± 2.32 |
| G3-C-196 (200 mg/kg) | 52.43 ± 3.98* |
| G4-C-197 (100 mg/kg) | 50.71 ± 2.38 |
| G5-C-197 (200 mg/kg) | 42.79 ± 2.75 |
| G6-C-198 (100 mg/kg) | 52.64 ± 2.10* |
| G7-C-198 (200 mg/kg) | 57.57 ± 4.43*** |
| G8-C-199 (200 mg/kg) | 51.50 ± 2.40* |

Data are expressed as mean ± S.E.M of seven rats per group.

We claim:

1. A synergistic herbal composition comprising:
   a first testosterone booster ingredient selected from the group consisting of water, aqueous alcohol, or alcohol extracts of *Punica granatum* fruit rind, *Cinnamomum zeylanicum* bark, *Nigella sativa* seeds and/or fruit, *Brassica nigra* seeds, and *Mangifera indica* stem bark or leaves; and
   at least one second testosterone booster ingredient selected from the group consisting of water, aqueous alcohol, or alcohol extracts of Punica granatum fruit rind, *Cinnamomum zeylanicum* bark, *Nigella sativa* seeds and/or fruit, *Brassica nigra* seeds, and *Mangifera indica* stem bark or leaves, wherein:

the second testosterone booster ingredient does not include the first testosterone booster ingredient; and the first and second testosterone booster ingredients are used in a ratio of from 1:3 to 3:1 by weight.

2. The synergistic herbal composition as claimed in claim 1, wherein the testosterone booster ingredients are present in an amount effective to treat low levels of testosterone.

3. The synergistic herbal composition as claimed in claim 1, wherein the synergistic composition further comprise at least one additional component selected from the group consisting of biological agent(s); pharmaceutically acceptable active ingredients, vitamins, minerals; pharmaceutically or nutraceutically or dietically acceptable excipients, carriers, and diluents.

4. The synergistic composition as claimed in claim 3, wherein the pharmaceutically or nutraceutically or dietically acceptable excipients, carriers and diluents are selected from the group consisting of glucose, fructose, sucrose, maltose, yellow dextrin, white dextrin, aerosil, microcrystalline cellulose, neusilin, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, animal and vegetable oils, white soft paraffin, paraffin, flavorants, colourants and wax.

5. The synergistic composition as claimed in claim 3, wherein the composition can be formulated into a dosage form selected from the group consisting of a dry powder form, a liquid form, a beverage, a food product, a dietary supplement, a tablet, a capsule, a soft chewable tablet, and a gummy bear.

6. The synergistic composition as claimed in claim 3, wherein the composition can be formulated into a food product, the food product being a solid food, a chocolate bar, a nutritional bar, a semisolid food, a cream, a jam, a gel, a beverage, a lactic acid bacteria beverage, a drop, a candy, a chewing gum, a gummy candy, a yoghurt, an ice cream, a pudding, a soft adzuki bean jelly, a jelly, a cookie, a tea, a soft drink, a juice, a milk, a coffee, a cereal, or a snack bar.

7. The synergistic composition as claimed in claim 1, wherein each of the extracts is obtained from at least one plant part selected from the group consisting of leaves, stems, tender stems, tender twigs, aerial parts, whole fruit, fruit rind, seed, root, bark, bulb, hardwood, a whole plant, and mixtures thereof.

8. The synergistic herbal composition as claimed in claim 1, wherein each of the extracts is produced using at least one solvent selected from the group consisting of C1-C5 alcohols; water; and mixtures thereof.

9. A method of increasing the testosterone levels, or treating/alleviating low levels of testosterone in a human subject, wherein the method comprises treating the human subject with an effective dose of the synergistic herbal composition of claim 1.

10. The synergistic herbal composition as claimed in claim 1, further comprising an aromatase inhibitor ingredient comprising at least one extract of an aromatase inhibitor herb selected from the group consisting of *Allium cepa, Tamarindus indica*, and *Cinnamomum tamala*.

11. The synergistic herbal composition as claimed in claim 1, wherein each of the extracts is produced using at least one solvent selected from the group consisting of ethanol, methanol, n-propanol, isopropyl alcohol, water, and mixtures thereof.

12. The synergistic herbal composition as claimed in claim 1, wherein:

the first testosterone booster ingredient is a water, aqueous alcohol, or alcohol extract of *Punica granatum* fruit rind; and the second testosterone booster ingredient is a water, aqueous alcohol, or alcohol extract of *Cinnamomum zeylanicum* bark, *Nigella sativa* seeds and/or fruit, *Brassica nigra* seeds, *Mangifera indica* stem bark, or *Mangifera indica* leaves.

13. The synergistic herbal composition as claimed in claim 1, wherein:

the first testosterone booster ingredient is a water, aqueous alcohol, or alcohol extract of *Cinnamomum zeylanicum* bark; and the second testosterone booster ingredient is a water, aqueous alcohol, or alcohol extract of *Nigella sativa* seeds and/or fruit, *Brassica nigra* seeds, *Mangifera indica* stem bark, or *Mangifera indica* leaves.

14. The synergistic herbal composition as claimed in claim 1, wherein:

the first testosterone booster ingredient is a water, aqueous alcohol, or alcohol extract of *Nigella sativa* seeds and/or fruit; and the second testosterone booster ingredient is a water, aqueous alcohol, or alcohol extract of *Brassica nigra* seeds, *Mangifera indica* stem bark, or *Mangifera indica* leaves.

15. The synergistic herbal composition as claimed in claim 1, wherein:

the first testosterone booster ingredient is a water, aqueous alcohol, or alcohol extract of *Brassica nigra* seeds; and the second testosterone booster ingredient is a water, aqueous alcohol, or alcohol extract of *Mangifera indica* stem bark or *Mangifera indica* leaves.

\* \* \* \* \*